(12) United States Patent
Rao et al.

(10) Patent No.: US 10,487,115 B2
(45) Date of Patent: Nov. 26, 2019

(54) PROTEINACEOUS COMPOUNDS AND USES THEREFOR

(71) Applicant: UNIVERSITY OF CANBERRA, Bruce, Australian Capital Territory (AU)

(72) Inventors: Sudha Rao, Deakin (AU); Peter Milburn, O'Connor (AU)

(73) Assignee: UNIVERSITY OF CANBERRA, Bruce, Australian Capital Territory (AU)

( * ) Notice: Subject to any disclaimer, the term of this patent is extended or adjusted under 35 U.S.C. 154(b) by 0 days.

(21) Appl. No.: 16/074,690

(22) PCT Filed: Feb. 1, 2017

(86) PCT No.: PCT/AU2017/050083
§ 371 (c)(1),
(2) Date: Aug. 1, 2018

(87) PCT Pub. No.: WO2017/132728
PCT Pub. Date: Aug. 10, 2017

(65) Prior Publication Data
US 2019/0040103 A1 Feb. 7, 2019

(30) Foreign Application Priority Data
Feb. 1, 2016 (AU) ................. 2016900314

(51) Int. Cl.
| | | |
|---|---|---|
| *A61K 31/00* | (2006.01) | |
| *C07K 7/08* | (2006.01) | |
| *A61P 35/00* | (2006.01) | |
| *A61K 38/17* | (2006.01) | |
| *A61K 38/43* | (2006.01) | |
| *A61K 38/00* | (2006.01) | |

(52) U.S. Cl.
CPC ............... *C07K 7/08* (2013.01); *A61K 38/17* (2013.01); *A61K 38/43* (2013.01); *A61P 35/00* (2018.01); *A61K 38/00* (2013.01)

(58) Field of Classification Search
CPC ..... A61K 31/00; A61P 35/00; C07K 14/4703; C07K 14/4702; C07K 16/40; G01N 33/574; G01N 33/56966; G01N 33/573; G01N 2333/4704
See application file for complete search history.

(56) References Cited

FOREIGN PATENT DOCUMENTS

| WO | 2000036083 A2 | 6/2000 | |
|---|---|---|---|
| WO | WO2004076654 A1 * | 9/2004 | ............... C12N 9/12 |
| WO | 2015039187 A1 | 3/2015 | |
| WO | 2016029262 A1 | 3/2016 | |

OTHER PUBLICATIONS

Belguise, K., et al., "The PKCθ Pathway Participates in the Aberrant Accumulation of Fra-1 Protein in Invasive ER-Negative Breast Cancer Cells," Oncogene, 31: 4889-4897 (2012).
Chand, S., et al., "Protein Kinase C-theta Inhibitors: A Novel Therapy for Inflammatory Disorders," Current Pharmaceutical Design, 18(30): 4725-4746 (2012).
DeVries, T.A., et al., "Nuclear import of PKCδ is Required for Apoptosis: Identification of a Novel Nuclear Import Sequence," The EMBO Journal, 21(22): 6050-6060 (2002).
He, Y.Q., et al., "The Endoglycosidase Heparanase Enters the Nucleus of T Lymphocytes and Modulates H3 Methylation at Actively Transcribed Genes via the Interplay with Key Chromatin Modifying Enzymes," Transcription, vol. 3(3): 130-145 (2012).
Jans, D.A. et al., "Nuclear Targeting Signal Recognition: A Key Control Point in Nuclear Transport?," BioEssays, 22: 532-544 (2000).
Kosugi, S., et al., "Design of Peptide Inhibitors for the Importin α/β Nuclear Import Pathway by Activity-Based Profiling," Chemistry & Biology, 15: 940-949 (2008).
Lim, P.S., et al., "Protein Kinase C in the Immune System: from Signalling to Chromatin Regulation," Immunology, 146: 508-522 (2015).
Mochly-Rosen, D., et al., "Protein Kinase C, an Elusive Therapeutic Target?," Nature Reviews: Drug Discovery, 11: 937-957 (2012).
Sutcliffe, E.L., et al., "Chromatin-Associated Protein Kinase C-θ Regulates an Inducible Gene Expression Program and MicroRNAs in Human T Lymphocytes," Molecular Cell, 41: 704-719 (2011).
Sutcliffe, E.L., et al., "Chromatinized Protein Kinase C-θ: Can it Escape the Clutches of NF-kB?," Frontiers in Immunology, 3:260, pp. 1-13 (2012).
Zafar, A., et al., "Chromatinized Protein Kinase C--θ Directly Regulates Inducible Genes in Epithelial to Mesenchymal Transition and Breast Cancer Stem Cells," Molecular and Cellular Biology, 34(16): 2961-2980 (2014).
International Search Report in corresponding International Patent Application No. PCT/AU2017/050083, dated Mar. 27, 2017 (3 pages).
Zafar et al., Genomics Data, vol. 3: 28-32 (2015).

* cited by examiner

*Primary Examiner* — Marcela M Cordero Garcia
*Assistant Examiner* — Jia-Hai Lee
(74) *Attorney, Agent, or Firm* — Edell, Shapiro & Finnan, LLC.

(57) ABSTRACT

Disclosed are proteinaceous molecules and their use in conditions associated with PKC-θ overexpression, such as cancer. More particularly, the present invention discloses proteinaceous molecules and their use in altering at least one of (i) formation; (ii) proliferation; (iii) maintenance; (iv) epithelial to mesenchymal cell transition; or (v) mesenchymal to epithelial cell transition of a PKC-θ overexpressing cell.

29 Claims, 20 Drawing Sheets
Specification includes a Sequence Listing.

PROTEINACEOUS COMPOUNDS AND USES THEREFOR

This application is a National Stage Entry of PCT/AU2017/050083, filed Feb. 1, 2017, which claims priority to Australian Patent Application No. 2016900314, filed Feb. 1, 2016, the contents of each of which are hereby incorporated by reference in their entireties. This application also contains a sequence listing submitted electronically via EFS-web, which serves as both the paper copy and the computer readable form (CRF) and consists of a file entitled "SeqListing_3950_0007C", which was created on Aug. 1, 2018, which is 17,420 bytes in size, and which is also incorporated by reference in its entirety.

FIELD OF THE INVENTION

This invention relates to proteinaceous molecules and their use in conditions associated with PKC-θ overexpression, such as cancer. More particularly, the present invention relates to proteinaceous molecules and their use in altering at least one of (i) formation; (ii) proliferation; (iii) maintenance; (iv) epithelial to mesenchymal cell transition; or (v) mesenchymal to epithelial cell transition of a PKC-θ overexpressing cell.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

Protein Kinase C's (PKCs) are a family of kinases which phosphorylate serine and threonine residues on a large number of proteins, thereby regulating a number of cellular responses. There are 11 isoforms which are subdivided into classical isoforms including PKC-α, -βI, -βII and -γ, which are diacylglycerol- and calcium-dependent; novel isoforms including PKC-δ, -ε, -η and -θ, which are diacylglycerol-dependent; and atypical isoforms including PKC-λ, ι and -ζ, which are diacylglycerol- and calcium-independent.

Over recent years, the PKC-θ isoform has increasingly been recognized as a promising therapeutic target for various conditions. PKC-θ plays a major role in the function of the immune system through the control of T-cell function. PKC-θ translocates to the nucleus from the cytoplasm where it influences inducible immune responsive gene transcription and microRNAs essential for an effective immune response in T-cells. Dysregulation of PKC-θ has been shown to be involved in inflammatory disorders, tumor progression and metastasis. PKC-θ activity has also been shown to be involved in various neurological, vascular and airway disorders. More recently, PKC-θ dysregulation has been linked to aggressive breast cancers and PKC-θ has been shown to play a role in the induction of epithelial to mesenchymal cell transition (EMT) and formation of breast cancer stem cells (CSCs) (Zafar, et al. (2014) *Mol Cell Biol*, 34(36): 2961-2980; Lim, et al. (2015) *Immunology*, 146: 508-522).

Due to the involvement of PKC-θ in inflammatory disorders and tumor formation and progression, PKC-θ is a promising therapeutic target. Whilst there are several PKC-θ inhibitors in development, notably sotrastaurin, which is currently undergoing trials for psoriasis and organ transplantation, these inhibitors typically suffer from a lack of selectivity for PKC-θ over the other PKC enzymes. Due to the large number of cellular responses mediated by the PKC enzymes, selective PKC-θ inhibition is highly desired (Lim, et al. (2015) *Immunology*, 146: 508-522; Manicassamy (2009) *Curr Opin Investig Drugs*, 10(11): 1225-1235).

Accordingly, there exists a need for new therapeutic agents that inhibit PKC-θ and which may be useful in conditions associated with PKC-θ overexpression, such as cancer.

SUMMARY OF THE INVENTION

The present invention is predicated in part on the discovery that proteinaceous molecules based on a subsequence of the PKC-θ polypeptide and structurally-related molecules inhibit PKC-θ activity, including translocation of PKC-θ into the nucleus of a cell. These molecules have also been shown to have significant activity in inhibiting EMT, in inhibiting formation and maintenance of CSC and non-CSC tumor cells, and in inducing mesenchymal to epithelial cell transition (MET), which makes them useful therefore in treating a range of conditions associated with PKC-θ overexpression, such as cancer.

In one aspect of the present invention, there is provided a method of altering at least one of (i) formation; (ii) proliferation; (iii) maintenance; (iv) epithelial to mesenchymal cell transition; or (v) mesenchymal to epithelial cell transition of a PKC-θ overexpressing cell, comprising contacting said PKC-θ overexpressing cell with an isolated or purified proteinaceous molecule represented by Formula I:

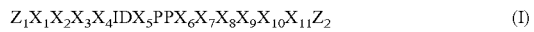

wherein:
"$Z_1$" and "$Z_2$" are independently absent or are independently selected from at least one of a proteinaceous moiety comprising from about 1 to about 50 amino acid residues (and all integer amino acid residues therebetween), and a protecting moiety;
"$X_1$" is absent or is selected from basic amino acid residues including R, K and modified forms thereof;
"$X_2$" and "$X_3$" are independently selected from basic amino acid residues including R, K and modified forms thereof;
"$X_4$" is selected from charged amino acid residues including R, K, D, E and modified forms thereof;
"$X_5$" is absent or is W or modified forms thereof;
"$X_6$" is selected from aromatic or basic amino acid residues including F, Y, W, R, K and modified forms thereof;
"$X_7$" is selected from basic amino acid residues including R, K and modified forms thereof;
"$X_8$" is absent or is P or modified forms thereof;
"$X_9$" is selected from basic amino acid residues including R, K and modified forms thereof;
"$X_{10}$" is selected from hydrophobic residues including V, L, I, M and modified forms thereof and P and modified forms thereof;
"$X_{11}$" is selected from basic amino acid residues including R, K and modified forms thereof.

In another aspect of the present invention, there is provided a method of treating or preventing a cancer in a subject wherein the cancer comprises at least one PKC-θ overexpressing cell, comprising administering to the subject an isolated or purified proteinaceous molecule represented by Formula I as defined above.

In yet another aspect of the present invention, there is provided an isolated or purified proteinaceous molecule represented by Formula I:

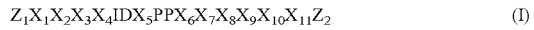

wherein:

"$Z_1$" and "$Z_2$" are independently absent or are independently selected from at least one of a proteinaceous moiety comprising from about 1 to about 50 amino acid residues (and all integer amino acid residues therebetween), and a protecting moiety;

"$X_1$" is absent or is selected from basic amino acid residues including R, K and modified forms thereof;

"$X_2$" and "$X_3$" are independently selected from basic amino acid residues including R, K and modified forms thereof;

"$X_4$" is selected from charged amino acid residues including R, K, D, E and modified forms thereof;

"$X_5$" is absent or is W or modified forms thereof;

"$X_6$" is selected from aromatic or basic amino acid residues including F, Y, W, R, K and modified forms thereof;

"$X_7$" is selected from basic amino acid residues including R, K and modified forms thereof;

"$X_8$" is absent or is P or modified forms thereof;

"$X_9$" is selected from basic amino acid residues including R, K and modified forms thereof;

"$X_{10}$" is selected from hydrophobic residues including V, L, I, M and modified forms thereof and P and modified forms thereof;

"$X_{11}$" is selected from basic amino acid residues including R, K and modified forms thereof; wherein the proteinaceous molecule is other than a proteinaceous molecule consisting of the amino acid sequence of SEQ ID NO: 1:

RKEIDPPFRPKVK. [SEQ ID NO: 1]

DETAILED DESCRIPTION OF THE INVENTION

1. Definitions

Figure 1:
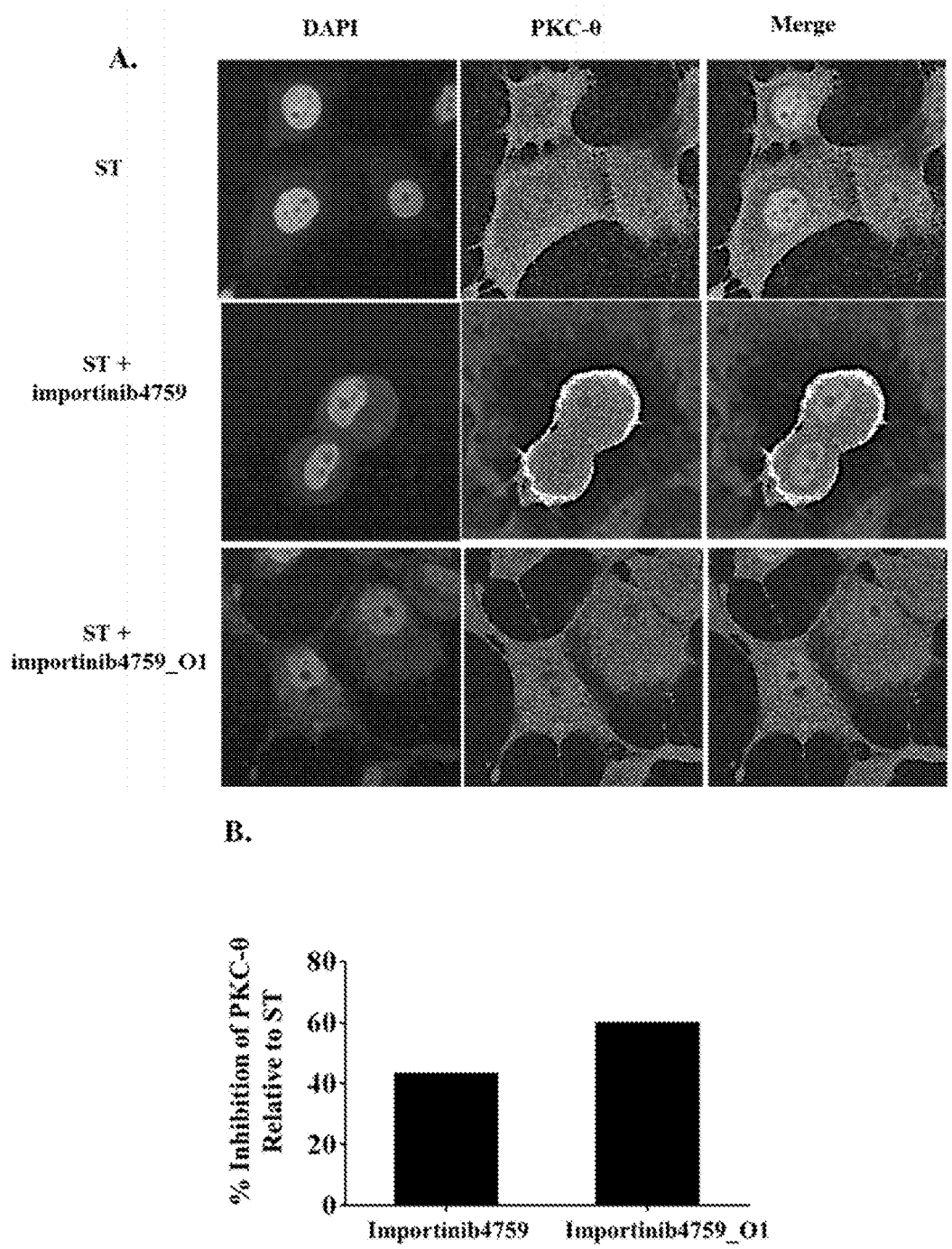
FIG. 1 Effect of importinib peptides on nuclear translocation of PKC-θ. (A) Representation of immunofluorescence microscopy pictures of MCF7 cells treated with importinib peptides; (B) Percentage of PKC-θ inhibition by impotinib peptides relative to control ST (stimulated) samples in human breast MCF7-IM model, calculated based on an average density of >50 cells using ImageJ software (importinib4759 and importinib4759_O1 have a p-value of ≤0.0001 relative to ST); (C) and (D) Representation of immunofluorescence microscopy pictures (left) and the plot of Fn/c (ratio of nuclear to cytoplasmic fluorescent intensity; right) showing the effect of importinib4759_O1 treatment on PKC-θ, PKC-β2, PKC-α, Imp 8 and Imp α2 localization. – represents stimulated control; + represents stimulated samples that pre-treated with importinib4759_O1. ****=p-value of ≤0.0001; ns=p-value of ≥0.05.
Figure 1:
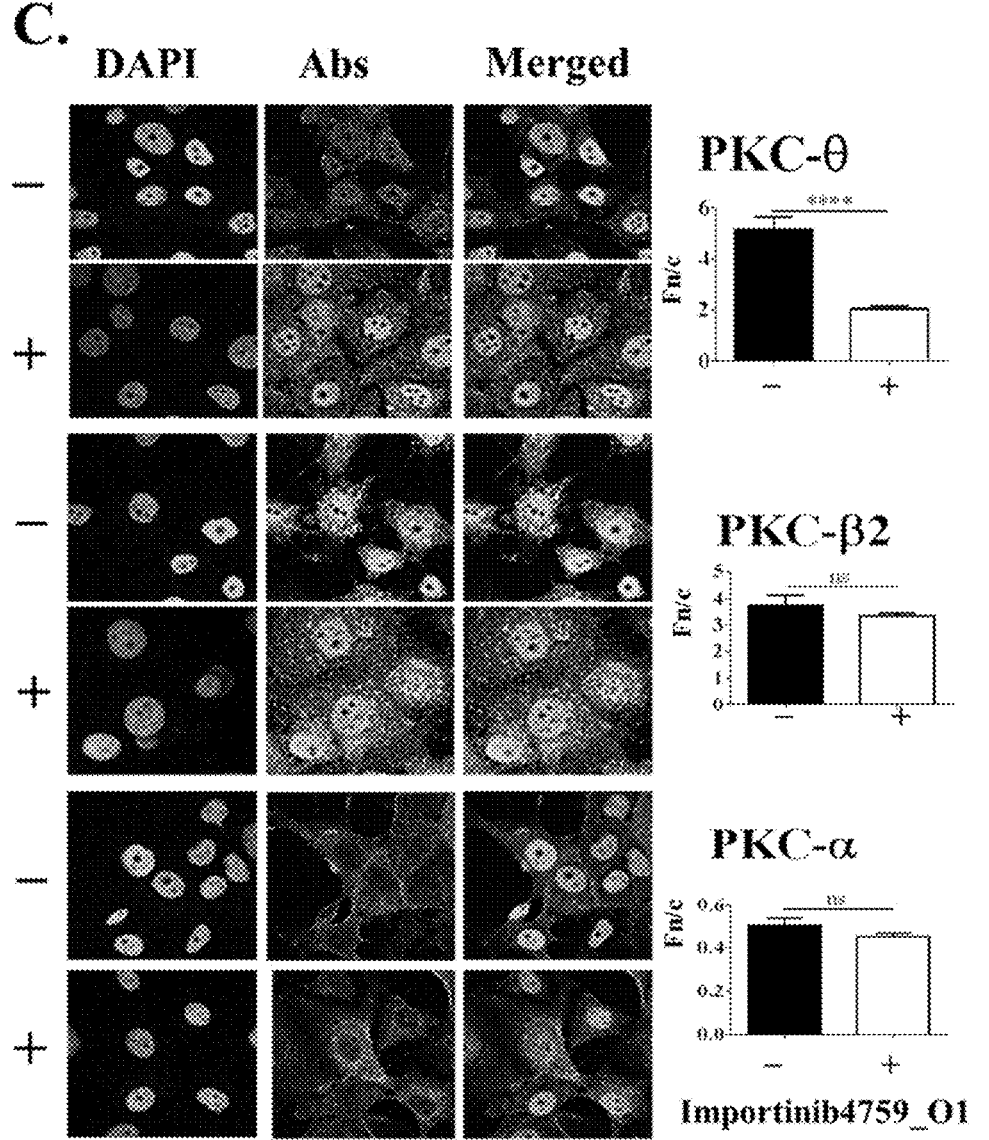
Figure 1:
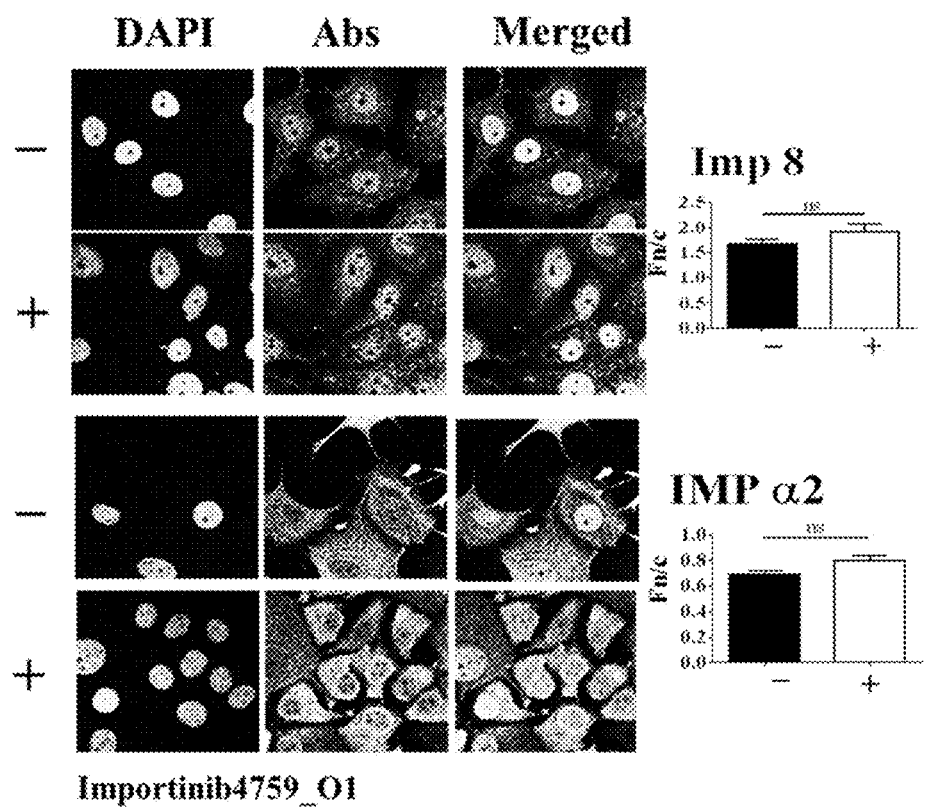

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

The terms "administration concurrently", "administering concurrently" or "administered concurrently" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters.

As used herein, the term "and/or" refers to and encompasses any and all possible combinations of one or more of the associated listed items, as well as the lack of combinations when interpreted in the alternative (or).

The term "cancer stem cell" (CSC) refers to a cell that has tumor-initiating and tumor-sustaining capacity, including the ability to extensively proliferate, form new tumors and maintain cancer development, i.e. cells with indefinite proliferative potential that drive the formation and growth of tumors. CSCs are biologically distinct from the bulk tumor cells and possess characteristics associated with stem cells, specifically the ability to self renew and to propagate and give rise to all cell types found in a particular cancer sample. The term "cancer stem cell" (CSC) includes both gene alteration in stem cells (SCs) and gene alteration in a cell which becomes a CSC. In specific embodiments, the CSCs are breast CSCs, which are suitably $CD24^+$ $CD44^+$, illustrative examples of which include $CD44^{high}$ $CD24^{low}$.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. In specific embodiments, the term "consisting essentially of", in the context of a specific amino acid sequence disclosed herein, includes within its scope about 1 to about 50 optional amino acids (and all integer optional amino acids in between) upstream of the specific amino acid sequence and/or about 1 to about 50 optional amino acids (and all integer optional amino acids in between) downstream of the specific amino acid sequence.

As used herein, the term "dosage unit form" refers to physically discrete units suited as unitary dosages for the subject to be treated, each unit containing a predetermined quantity of active material calculated to produce the desired therapeutic effect in association with the required pharmaceutically acceptable vehicle.

The term "enzymatic activity" as used herein in relation to PKC-θ refers to the phosphorylation of a serine and/or threonine residue on a protein.

As used herein, the term "epithelial-to-mesenchymal transition" (EMT) refers to the conversion from an epithelial cell to a mesenchymal phenotype, which is a normal process of embryonic development. EMT is also the process whereby injured epithelial cells that function as ion and fluid transporters become matrix remodeling mesenchymal cells, in carcinomas, this transformation typically results in altered cell morphology, the expression of mesenchymal proteins and increased invasiveness. The criteria for defining EMT in vitro involve the loss of epithelial cell polarity, the separation into individual cells and subsequent dispersion after the acquisition of cell motility (refer to Vincent-Salomon and Thiery, *Breast Cancer Res.* 2003; 5(2):101-6). Classes of molecules that change in expression, distribution and/or function during EMT, and that are causally involved, include growth factors (e.g. transforming growth factor (TGF)-β, wnts), transcription factors (e.g. SNAI, SMAD, LEF and nuclear β-catenin), molecules of the cell-to-cell adhesion axis (cadherins, catenins), cytoskeletal modulators (Rho family) and extracellular proteases (matrix metalloproteinases, plasminogen activators) (refer to Thompson and Newgreen, *Cancer Res.* 2005; 65(14):5991-5).

As used herein, the term "epithelium" refers to the covering of internal and external surfaces of the body, including the lining of vessels and other small cavities. It consists of a collection of epithelial cells forming a relatively thin sheet or layer due to the constituent cells being mutually and extensively adherent laterally by cell-to-cell junctions. The layer is polarized and has apical and basal sides. Despite the tight regimentation of the epithelial cells, the epithelium does have some plasticity and cells in an epithelial layer can alter shape, such as change from flat to columnar or pinch in at one end and expand at the other. However, these tend to occur in cell groups rather than individually (refer to Thompson and Newgreen, *Cancer Res.* 2005; 65(14):5991-5).

The term "expression" refers the biosynthesis of a gene product. For example, in the case of a coding sequence, expression involves transcription of the coding sequence into mRNA and translation of mRNA into one or more polypeptides. Conversely, expression of anon-coding sequence involves transcription of the non-coding sequence into a transcript only. The term "expression" is also used herein to refer to the presence of a protein or molecule in a particular location and, thus, may be used interchangeably with "localization".

The term "host cell" includes an individual cell or cell culture which can be or has been a recipient of any recombinant vector(s) or isolated polynucleotide of the invention. Host cells include progeny of a single host cell and the progeny may not necessarily be completely identical (in morphology or in total DNA complement) to the original parent cell due to natural, accidental or deliberate mutation and/or change. A host cell includes cells transfected or infected in vivo or in vitro with a recombinant vector or a polynucleotide of the invention. A host cell which comprises a recombinant vector of the invention is a recombinant host cell.

As used herein, the term "isolated" refers to material that is substantially or essentially free from components that normally accompany it in its native state. For example, an "isolated proteinaceous molecule" refers to in vitro isolation and/or purification of a proteinaceous molecule from its natural cellular environment and from association with other components of the cell. "Substantially free" means that a preparation of proteinaceous molecule is at least 10, 15, 20, 25, 30, 35, 40, 45, 50, 55, 60, 65, 70, 75, 80, 85, 90, 91, 92, 93, 94, 95, 96, 97, 98 or 99% pure. In a preferred embodiment, the preparation of proteinaceous molecule has less than about 30, 25, 20, 15, 10, 9, 8, 7, 6, 5, 4, 3, 2 or 1% (by dry weight), of molecules that are not the subject of this invention (also referred to herein as a "contaminating molecules"). When the proteinaceous molecule is recombinantly produced, it is also desirably substantially free of culture medium, i.e., culture medium represents less than about 20, 15, 10, 5, 4, 3, 2 or 1% of the volume of the preparation. The invention includes isolated or purified preparations of at least 0.01, 0.1, 1.0, and 10 milligrams in dry weight.

As used herein, the term "mesenchymal-to-epithelial transition" (MET) is a reversible biological process that involves the transition from motile, multipolar or spindle-shaped mesenchymal cells to planar arrays of polarized cells called epithelia. MET is the reverse process of EMT. METs occur in normal development, cancer metastasis and induced pluripotent stem cell reprogramming.

As used herein, the term "mesenchyme" refers to the part of the embryonic mesoderm, consisting of loosely packed, unspecialized cells set in a gelatinous ground substance, from which connective tissue, bone, cartilage and the circulatory and lymphatic systems develop. Mesenchyme is a collection of cells which form a relatively diffuse tissue network. Mesenchyme is not a complete cellular layer and the cells typically have only points on their surface engaged in adhesion to their neighbors. These adhesions may also involve cadherin association (see Thompson and Newgreen, *Cancer Res.* 2005; 65(14):5991-5).

As used herein, the terms "overexpress," "overexpression", "overexpressing" or "overexpressed" interchangeably refer to a gene (e.g. PKC-θ gene) that is transcribed or translated at a detectably greater level, usually in a cancer cell, in comparison to a normal cell. Overexpression, therefore, refers to both overexpression of protein and RNA (due to increased transcription, post transcriptional processing, translation, post translational processing, altered stability and altered protein degradation), as well as local overexpression due to altered protein traffic patterns (increased nuclear localization) and augmented functional activity, for example, as in an increased enzyme hydrolysis of substrate. Overexpression can also be by 10%, 20%, 30%, 40%, 50%, 60%, 70%, 80%, 90% or more in comparison to a normal cell or comparison cell (e.g. a breast cell).

The term "operably linked" as used herein means placing a structural gene under the regulatory control of a regulatory element including, but not limited to, a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

The term "PKC-θ inhibitor" and grammatical variants thereof are used herein to refer to a molecule that decreases or inhibits at least one function or biological activity of PKC-θ. For example, PKC-θ inhibitors may inhibit or reduce the nuclear translocation of PKC-θ, may inhibit or reduce the enzymatic activity of PKC-θ and/or may inhibit or reduce the expression of PKC-θ. In some embodiments, the term "PKC-θ inhibitor" refers to a molecule that inhibits the nuclear translocation of PKC-θ.

As used herein, the term "PKC-θ overexpressing cell" refers to a vertebrate cell, particularly a mammalian or avian cell, especially a mammalian cell, that expresses PKC-θ at a detectably greater level than a normal cell. The cell may be a vertebrate cell, such as a primate cell; an avian cell; a livestock animal cell such as a sheep cell, cow cell, horse cell, deer cell, donkey cell and pig cell; a laboratory test animal cell such as a rabbit cell, mouse cell, rat cell, guinea pig cell and hamster cell; a companion animal cell such as a cat cell and dog cell; and a captive wild animal cell such as a fox cell, deer cell and dingo cell. In particular embodiments, the PKC-θ overexpressing cell is a human cell. In specific embodiments, the PKC-θ overexpressing cell is a cancer stem cell or a non-cancer stem cell tumor cell; preferably a cancer stem cell tumor cell. Overexpression can also be by 10%, 20%, 30%, 40%, 50%, 60%, 70%, 80%, 90% or more in comparison to a normal cell or comparison cell (e.g. a breast cell).

As used herein, the terms "polypeptide," "proteinaceous molecule," "peptide" and "protein" are used interchangeably to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogues of an amino acid including, for example, unnatural amino acids or polypeptides with substituted linkages.

The term "selective" and grammatical variants thereof are used herein to refer to molecules that inhibit PKC-θ without substantially inhibiting the function of one or more other PKC enzyme or isoform, such as PKC-α, PKC-θ, PKC-γ, PKC-δ, PKC-ε, PKC-ζ, PKC-η, PKC-λ, PKC-μ, or PKC-ν. Generally, a molecule that is selective for PKC-θ exhibits PKC-θ selectivity of greater than about 2-fold, 5-fold, 10-fold, 20-fold, 50-fold or greater than about 100-fold with respect to inhibition of one or more other PKC enzyme (i.e. a PKC other than PKC-θ, such as PKC-α, PKC-θ, PKC-γ, PKC-δ, PKC-ε, PKC-ζ, PKC-η, PKC-λ, PKC-μ, or PKC-ν). In other embodiments, selective molecules display at least 50-fold greater inhibition towards PKC-θ than towards one or more other PKC enzyme. In further embodiments, selective molecules display at least 100-fold greater inhibition towards PKC-θ than towards one or more other PKC enzyme. In still further embodiments, selective molecules display at least 500-fold greater inhibition towards PKC-θ than towards one or more other PKC enzyme. In yet further embodiments, selective molecules display at least 100-fold greater inhibition towards PKC-θ than towards one or more other PKC enzyme.

As used herein, the terms "salts" and "prodrugs" include any pharmaceutically acceptable salt, ester, hydrate or any other compound which, upon administration to the recipient, is capable of providing (directly or indirectly) a proteinaceous molecule of the invention, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl and butyl chlorides, bromides and iodides; dialkyl sulfates such as dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs can be carried out by methods known in the art. For example, metal salts can be prepared by reaction of a compound of the invention with a metal hydroxide. An acid salt can be prepared by reacting an appropriate acid with a proteinaceous molecule of the invention.

The term "stringency" as used herein, refers to the temperature and ionic strength conditions, and presence or absence of certain organic solvents during hybridization and washing procedures. The higher the stringency, the higher will be the degree of complementarity between immobilized target nucleotide sequences and the labelled probe polynucleotide sequences that remain hybridized to the target after washing. The term "high stringency" refers to temperature and ionic conditions under which only nucleotide sequences having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "subject" as used herein refers to a vertebrate subject, particularly a mammalian or avian subject, for whom therapy or prophylaxis is desired. Suitable subjects include, but are not limited to, primates; avians; livestock animals such as sheep, cows, horses, deer, donkeys and pigs; laboratory test animals such as rabbits, mice, rats, guinea pigs and hamsters; companion animals such as cats and dogs; and captive wild animals such as foxes, deer and dingoes. In particular, the subject is a human. However, it will be understood that the aforementioned terms do not imply that symptoms are present.

As used herein, the term "tumor" refers to any neoplastic cell growth and proliferation, whether malignant or benign, and all pre-cancerous and cancerous cells and tissues. The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. The term "precancerous" refers to a condition or a growth that typically precedes or develops into a cancer. The term "non-metastatic" refers to a cancer that is benign or that remains at the primary site and has not penetrated into the lymphatic or blood vessel system or to tissues other than the primary site. Generally, a non-metastatic cancer is any cancer that is a Stage 0, I or II cancer. By "early stage cancer" is meant a cancer that is not invasive or metastatic or is classified as a Stage 0, I or II cancer. The term "late stage cancer" generally refers to a Stage III or IV cancer, but can also refer to a Stage II cancer or a substage of a Stage II cancer. One skilled in the art will appreciate that the classification of a Stage II cancer as either an early stage cancer or a late stage cancer depends on the particular type of cancer. Illustrative examples of cancer include, but are not limited to, breast cancer, prostate cancer, ovarian cancer, cervical cancer, pancreatic cancer, colorectal cancer, lung cancer, hepatocellular cancer, gastric cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, mesothelioma, rectal cancer and esophageal cancer. In an exemplary embodiment, the cancer is breast cancer.

As used herein, the term "vector" refers to a polynucleotide molecule, suitably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e. a vector that exists as an extra-chromosomal entity, the replication of which is independent of chromosomal replication, e.g. a linear or closed circular plasmid, an extra-chromosomal element, a mini-chromosome or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in fungi, bacterial or animal cells, preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

Each embodiment described herein is to be applied mutatis mutandis to each and every embodiment unless specifically stated otherwise.

2. Proteinaceous PKC-θ Inhibitors

The present invention is based, in part, on the identification of proteinaceous molecules that inhibit the nuclear translocation of PKC-θ. Such proteinaceous molecules inhibit formation and maintenance of CSC and non-CSC tumor cells, inhibit EMT and induce MET of CSC tumor cells. Thus, the inventors conceived that the proteinaceous molecules of the invention may be used for the treatment or prevention of cancer.

Accordingly, in one aspect of the present invention, there is provided an isolated or purified proteinaceous molecule represented by Formula I:

$$Z_1X_1X_2X_3X_4IDX_5PPX_6X_7X_8X_9X_{10}X_{11}Z_2 \qquad (I)$$

wherein:
"$Z_1$" and "$Z_2$" are independently absent or are independently selected from at least one of a proteinaceous moiety comprising from about 1 to about 50 amino acid residues (and all integer amino acid residues therebetween), and a protecting moiety;
"$X_1$" is absent or is selected from basic amino acid residues including R, K and modified forms thereof;
"$X_2$" and "$X_3$" are independently selected from basic amino acid residues including R, K and modified forms thereof;
"$X_4$" is selected from charged amino acid residues including R, K, D, E and modified forms thereof;
"$X_5$" is absent or is W or modified forms thereof;
"$X_6$" is selected from aromatic or basic amino acid residues including F, Y, W, R, K and modified forms thereof;
"$X_7$" is selected from basic amino acid residues including R, K and modified forms thereof;
"$X_8$" is absent or is P or modified forms thereof;
"$X_9$" is selected from basic amino acid residues including R, K and modified forms thereof;
"$X_{10}$" is selected from hydrophobic residues including V, L, I, M and modified forms thereof and P and modified forms thereof;
"$X_{11}$" is selected from basic amino acid residues including R, K and modified forms thereof.

In some embodiments, "$X_1$" to "$X_{11}$" are selected from a combination of one or more of the following:
"$X_1$" is absent or is R;
"$X_2$" is R;
"$X_3$" is K;
"$X_4$" is E or R;
"$X_5$" is absent or is W;
"$X_6$" is F or R;
"$X_7$" is R;
"$X_8$" is absent or is P;
"$X_9$" is K;
"$X_{10}$" is V or P; and
"$X_{11}$" is K.

In some embodiments, "$Z_1$" consists of 10, 9, 8, 7, 6, 5, 4, 3, 2 or 1 amino acid residues. In some embodiments, "$Z_2$" consists of 10, 9, 8, 7, 6, 5, 4, 3, 2 or 1 amino acid residues. In some embodiments, the amino acid residues in "$Z_1$" and "$Z_2$" are selected from any amino acid residue.

In some embodiments, "$Z_1$" is a proteinaceous molecule represented by Formula II:

$$X_{12}X_{13}X_{14}X_{15}X_{16} \qquad (II)$$

wherein:
"$X_{12}$" is absent or is a protecting moiety;
"$X_{13}$" is absent or is selected from P and basic amino acid residues including R, K and modified forms thereof;
"$X_{14}$" is absent or is selected from P and basic amino acid residues including R, K and modified forms thereof;
"$X_{15}$" is absent or is selected from P and basic amino acid residues including R, K and modified forms thereof;
"$X_{16}$" is absent or is selected from P and basic amino acid residues including R, K and modified forms thereof.

In some embodiments, "$Z_2$" is a proteinaceous molecule represented by Formula III:

$$X_{17}X_{18}X_{19}X_{20} \qquad (III)$$

wherein:

"$X_{17}$" is absent or is selected from any amino acid residue;
"$X_{18}$" is absent or is selected from any amino acid residue;
"$X_{19}$" is absent or is selected from any amino acid residue;
"$X_{20}$" is absent or is a protecting moiety.

In some embodiments, "$Z_1$" and "$Z_2$" are absent.

In particular embodiments, the proteinaceous molecule of Formula I comprises, consists or consists essentially of an amino acid sequence represented by SEQ ID NO: 1 or 2:

```
                                              [SEQ ID NO: 1]
                RKEIDPPFRPKVK
                or

[SEQ ID NO: 2]
                RRKRIDWPPRRKPK.
```

The proteinaceous molecule of SEQ ID NO: 1 is also referred to herein as "importinib4759" and the proteinaceous molecule of SEQ ID NO: 2 is also referred to herein as "importinib4759_O1".

In some embodiments, the proteinaceous molecule of Formula I is other than a proteinaceous molecule consisting of the amino acid sequence of SEQ ID NO: 1.

Thus, in particular embodiments, the proteinaceous molecule of Formula I comprises, consists or consists essentially of the amino acid sequence of SEQ ID NO: 2.

The present invention also contemplates proteinaceous molecules that are variants of SEQ ID NO: 1 and/or 2. Such "variant" proteinaceous molecules include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein.

Variant proteins encompassed by the present invention are biologically active, that is, they continue to possess the desired biological activity of the native protein. Such variants may result from, for example, genetic polymorphism or from human manipulation.

The proteinaceous molecules of SEQ ID NO: 1 and/or 2 may be altered in various ways including amino acid substitutions, deletions, truncations, and insertions. Methods for such manipulations are generally known in the art. For example, amino acid sequence variants of SEQ ID NO: 1 and/or 2 can be prepared by mutagenesis of nucleic acids encoding the amino acid sequence of SEQ ID NO: 1 and/or 2. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of the proteinaceous molecules of SEQ ID NO: 1 and/or 2. Recursive ensemble mutagenesis (REM), a technique which enhances the frequency of functional mutants in the libraries, can be used in combination with screening assays to identify active variants (Arkin and Yourvan (1992) *Proc. Natl. Acad. Sci. USA* 89: 7811-7815; Delgrave et al., (1993) *Protein Engineering*, 6: 327-331). Conservative substitutions, such as exchanging one amino acid with another having similar properties, may be desirable as discussed in more detail below.

Variant peptides or polypeptides of the invention may contain conservative amino acid substitutions at various locations along their sequence, as compared to a parent (e.g., naturally-occurring or reference) amino acid sequence, such as SEQ ID NO: 1 and/or 2. A "conservative amino acid substitution" is one in which the amino acid residue is replaced with an amino acid residue having a similar side chain. Families of amino acid residues having similar side chains have been defined in the art as discussed in detail below.

The amino acid sequence of the proteinaceous molecules of the invention is defined in terms of amino acids of certain characteristics or sub-classes. Amino acid residues are generally sub-classified into major sub-classes as follows:

Acidic: The residue has a negative charge due to loss of a proton at physiological pH and the residue is attracted by aqueous solution so as to seek the surface positions in the conformation of a peptide in which it is contained when the peptide is in aqueous medium at physiological pH. Amino acids having an acidic side chain include glutamic amid and aspartic acid.

Basic: The residue has a positive charge due to association with protons at physiological pH or within one or two pH units thereof (e.g. histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residue is charged at physiological pH and, therefore, includes amino acids having acidic or basic side chains, such as glutamic acid, aspartic acid, arginine, lysine and histidine.

Hydrophobic: The residue is not charged at physiological pH and the residue is repelled by aqueous solution so as to seek the inner positions in the conformation of a peptide in which it is contained when the peptide is in aqueous medium at physiological pH. Amino acids having a hydrophobic side chain include tyrosine, valine, isoleucine, leucine, methionine, phenylalanine and tryptophan.

Neutral/polar: The residues are not charged at physiological pH but the residue is not sufficiently repelled by aqueous solutions so that it would seek inner positions in the conformation of a peptide in which it is contained when the peptide is in aqueous medium at physiological pH. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g. PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (1992), *Science*, 256(5062): 1443-1445), however, include proline in the same group as glycine, serine, alanine and threonine. Accordingly, for the purposes of the present invention, proline is classified as a "small" amino acid.

The degree of attraction or repulsion required for classification as polar or non-polar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small amino acid residues are, of course, always non-aromatic. Dependent on their structural properties, amino acid residues may fall in two or more classes. For the naturally-occurring protein amino acids, sub-classification according to this scheme is presented in Table 1.

TABLE 3

Amino Acid Sub-Classification

| Sub-classes | Amino Acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/ neutral | Alanine, Glycine, Isoleucine, Leucine, Methionine, Phenylalanine, Proline, Tryptophan, Valine |
| Polar/ neutral | Asparagine, Histidine, Glutamine, Cysteine, Serine, Threonine, Tyrosine |
| Polar/ negative | Aspartic acid, Glutamic acid |
| Polar/ positive | Lysine, Arginine |
| Polar/ large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartic acid with a glutamic acid, a threonine with a serine, or a similar replacement of an amino acid with a structurally related amino acid will not have a major effect on the properties of the resulting variant peptide useful in the invention. Whether an amino acid change results in a proteinaceous molecule that inhibits PKC-θ can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 4

Exemplary and Preferred Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Nle | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Nle | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, *Biochemistry*, third edition, Wm.C. Brown Publishers (1993).

Thus, a predicted non-essential amino acid residue in a peptide of the invention is typically replaced with another amino acid residue from the same side chain family. Alternatively, mutations can be introduced randomly along all or part of the coding sequence of a peptide of the invention, such as by saturation mutagenesis, and the resultant mutants can be screened for an activity of the parent polypeptide, as described for example herein, to identify mutants which retain that activity. Following mutagenesis of the coding sequences, the encoded peptide can be expressed recombinantly and its activity determined. A "non-essential" amino acid residue is a residue that can be altered from the wild-type sequence of an embodiment peptide of the invention without abolishing or substantially altering one or more of its activities. Suitably, the alteration does not substantially alter one of these activities, for example, the activity is at least 20%, 40%, 60%, 70% or 80% of that of the wild-type. By contrast, an "essential" amino acid residue is a residue that, when altered from the wild-type sequence of an embodiment peptide of the invention, results in abolition of an activity of the parent molecule such that less than 20% of the wild-type activity is present. For example, such essential amino acid residues include Ile (or modified form thereof) at position 5, Asp (or modified form thereof) at position 6, Pro (or modified form thereof) at position 8 and Pro (or modified form thereof) at position 9, relative to the numbering of Formula I commencing at $X_1$.

Accordingly, the present invention also contemplates variants of the proteinaceous molecules of SEQ ID NO 1 and/or 2 of the invention, wherein the variants are distinguished from the parent sequence by the addition, deletion, or substitution of one or more amino acid residues. In general, variants will display at least about 80%, 81%, 82%, 83%, 84%, 85%, 86%, 87%, 88%, 89%, 90%, 91%, 92%, 93%, 94%, 95%, 96%, 97%, 98%, 99% sequence similarity to a parent or reference proteinaceous molecule sequence as, for example, set forth in SEQ ID NO: 1 or 2, as determined by sequence alignment programs described elsewhere herein using default parameters. Desirably, variants will have at least 80%, 81%, 82%, 83%, 84%, 85%, 86%, 87%, 88%, 89%, 90%, 91%, 92%, 93%, 94%, 95%, 96%, 97%, 98%, 99% sequence identity to a parent or reference peptide sequence as, for example, set forth in SEQ ID NO: 1 or 2, as determined by sequence alignment programs described herein using default parameters. Variants of importinib4759 and importinib4759_O1, which fall within the scope of a variant peptide of the invention, may differ from the parent molecule generally by at least 1, but by less than 5, 4, 3, 2 or 1 amino acid residue(s). In some embodiments, a variant peptide of the invention differs from the corresponding sequence in SEQ ID NO: 1 or 2 by at least 1, but by less than 5, 4, 3, 2 or 1 amino acid residue(s). In some embodiments, the amino acid sequence of the variant peptide of the invention comprises Ile (or modified form thereof) at position 5, Asp (or modified form thereof) at position 6, Pro (or modified form thereof) at position 8 and/or Pro (or modified form thereof) at position 9, relative to the numbering of Formula I commencing at $X_1$. In some embodiments, the amino acid sequence of the variant peptide of the invention comprises the proteinaceous molecule of Formula I. In particular embodiments, the variant peptide of the invention inhibits PKC-θ nuclear translocation.

If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution.

In some embodiments, calculations of sequence similarity or sequence identity between sequences are performed as follows:

To determine the percent identity of two amino acid sequences or of two nucleic acid sequences, the sequences are aligned for optimal comparison purposes (e.g. gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 40%, more usually at least 50% or 60%, and even more usually at least 70%, 80%, 90% or 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e. conservative substitution) at the corresponding position in the second sequence, then the molecules are similar at that position.

The percent identity between the two sequences is a function of the number of identical amino acid residues shared by the sequences at individual positions, taking into account the number of gaps and the length of each gap, which need to be introduced for optimal alignment of the two sequences. By contrast, the percent similarity between the two sequences is a function of the number of identical and similar amino acid residues shared by the sequences at individual positions, taking into account the number of gaps and the length of each gap, which need to be introduced for optimal alignment of the two sequences.

The comparison of sequences and determination of percent identity or percent similarity between sequences can be accomplished using a mathematical algorithm. In certain embodiments, the percent identity or similarity between amino acid sequences is determined using the Needleman and Wunsch, (1970, *J. Mol. Biol.*, 48: 444-453) algorithm which has been incorporated into the GAP program in the GCG software package (Devereaux, et al. (1984) *Nucleic Acids Research*, 12: 387-395), using either a Blosum 62 matrix or a PAM250 matrix, and a gap weight of 16, 14, 12, 10, 8, 6, or 4 and a length weight of 1, 2, 3, 4, 5, or 6. In some embodiments, the percent identity or similarity between amino acid sequences can be determined using the algorithm of Meyers and Miller (1989, *Cabios*, 4: 11-17) which has been incorporated into the ALIGN program (version 2.0), using a PAM120 weight residue table, a gap length penalty of 12 and a gap penalty of 4.

The present invention also contemplates an isolated, synthetic or recombinant peptide that is encoded by a polynucleotide sequence that hybridizes under stringency conditions as defined herein, especially under medium, high or very high stringency conditions, preferably under high or very high stringency conditions, to a polynucleotide sequence encoding the peptides of SEQ ID NO: 1 and/or 2 or the non-coding strand thereof. The invention also contemplates an isolated nucleic acid molecule comprising a polynucleotide sequence that hybridizes under stringency conditions as defined herein, especially under medium, high or very high stringency conditions, preferably under high or very high stringency conditions, to a polynucleotide sequence encoding the peptides of SEQ ID NO: 1 and/or 2 or the non-coding strand thereof.

As used herein, the term "hybridizes under stringency conditions" describes conditions for hybridization and washing and may encompass low stringency, medium stringency, high stringency and very high stringency conditions.

Guidance for performing hybridization reactions can be found in Ausubel, et al. (1998) Current Protocols in Molecular Biology (John Wiley and Sons, Inc.), in particular sections 6.3.1-6.3.6. Both aqueous and non-aqueous methods can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% sodium dodecyl sulfate (SDS) for hybridization at 65° C., and (i) 2× sodium chloride/sodium citrate (SSC), 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6×SSC at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 MNaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In some aspects of the present invention, there is provided an isolated, synthetic or recombinant peptide of the invention that is encoded by a polynucleotide sequence that hybridizes under high stringency conditions to a polynucleotide sequence encoding the peptides of SEQ ID NO: 1 and/or 2 or the non-coding strand thereof. In certain embodiments, the isolated, synthetic or recombinant peptide of the invention is encoded by a polynucleotide sequence that hybridizes under very high stringency conditions to a polynucleotide sequence encoding the peptides of SEQ ID NO: 1 and/or 2 or the non-coding strand thereof. One embodiment of very high stringency conditions includes hybridizing 0.5 M sodium phosphate, 7% SDS at 65° C., followed by one or more washes at 0.2×SSC, 1% SDS at 65° C. In some embodiments, the amino acid sequence of the variant peptide of the invention comprises Ile (or modified form thereof) at position 5, Asp (or modified form thereof) at position 6, Pro (or modified form thereof) at position 8 and/or Pro (or modified form thereof) at position 9, relative to the numbering of Formula I commencing at X$_1$. In some embodiments, the amino acid sequence of the variant peptide of the invention comprises the proteinaceous molecule of Formula I. In particular embodiments, the variant peptide of the invention inhibits PKC-θ nuclear translocation.

Other stringency conditions are well known in the art and a person skilled in the art will recognize that various factors can be manipulated to optimize the specificity of the hybridization. Optimization of the stringency of the final washes can serve to ensure a high degree of hybridization. For detailed examples, see Ausubel, et al. (1998) Current Protocols in Molecular Biology (John Wiley and Sons, Inc.), in particular pages 2.10.1 to 2.10.16 and Sambrook, et al. (1989) Molecular Cloning: A Laboratory Manual (Cold Spring Harbour Press), in particular Sections 1.101 to 1.104.

While stringent washes are typically carried out at temperatures from about 42° C. to 68° C., a person skilled in the art will appreciate that other temperatures may be suitable for stringent conditions. Maximum hybridization rate typically occurs at about 20° C. to 25° C. below the T$_m$ for formation of a DNA-DNA hybrid. It is well known in the art that the T$_m$ is the melting temperature, or temperature at which two complementary polynucleotide sequences dissociate. Methods for estimating T$_m$ are well known in the art (see Ausubel, et al. (1998) Current Protocols in Molecular Biology (John Wiley and Sons, Inc.) at page 2.10.8). In general, the T$_m$ of a perfectly matched duplex of DNA may be predicted as an approximation by the formula:

$$T_m = 81.5 + 16.6(\log_{10} M) + 0.41(\% \, G+C) - 0.63(\% \, \text{formamide}) - (600/\text{length})$$

wherein: M is the concentration of Nat, preferably in the range of 0.01 M to 0.4 M; % G+C is the sum of guanosine and cytosine bases as a percentage of the total number of bases, within the range between 30% and 75% G+C; % formamide is the percent formamide concentration by volume; length is the number of base pairs in the DNA duplex. The T$_m$ of a duplex DNA decreases by approximately 1° C. with every increase of 1% in the number of randomly mismatched base pairs. Washing is generally carried out at T$_m$-15° C. for high stringency, or T$_m$-30° C. for moderate stringency.

In one example of a hybridization procedure, a membrane (e.g. a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% BSA), 0.1% SDS and 200 mg/mL denatured salmon sperm DNA) containing labeled probe. The membrane is then subjected to two sequential medium stringency washes (i.e. 2×SSC, 0.1% SDS for 15 min at 45° C., followed by 2×SSC, 0.1% SDS for 15 min at 50° C.), followed by two sequential higher stringency washes (i.e. 0.2×SSC, 0.1% SDS for 12 min at 55° C. followed by 0.2×SSC and 0.1% SDS solution for 12 min at 65-68° C.

The proteinaceous molecules of the present invention also encompass peptides comprising amino acids with modified side chains, incorporation of unnatural amino acid residues and/or their derivatives during peptide synthesis and the use of cross-linkers and other methods which impose conformational constraints on the peptides of the invention. Examples of side chain modifications include modifications of amino groups, such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with sodium borohydride; reductive alkylation by reaction with an aldehyde followed by reduction with sodium borohydride; and trinitrobenzylation of amino groups with 2,4,6-trinitrobenzene sulfonic acid (TNBS).

The carboxyl group may be modified by carbodiimide activation through O-acylisourea formation followed by subsequent derivatization, for example, to a corresponding amide.

The guanidine group of arginine residues may be modified by formation of heterocyclic condensation products with reagents such as 2,3-butanedione, phenylglyoxal and glyoxal.

Tryptophan residues may be modified, for example, by alkylation of the indole ring with 2-hydroxy-5-nitrobenzyl bromide or sulfonyl halides, or by oxidation with N-bromosuccinimide.

Tyrosine residues may be modified by nitration with tetranitromethane to form 3-nitrotyrosine derivatives.

Examples of incorporating unnatural amino acids and derivatives during peptide synthesis include, but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine, selenocysteine and/or D-isomers of amino acids. A list of unnatural amino acids contemplated by the present invention is shown in Table 3.

TABLE 3

Exemplary Unnatural Amino Acids
Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-methylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvaline | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |

TABLE 3-continued

Exemplary Unnatural Amino Acids
Non-Conventional Amino Acids

| | |
|---|---|
| N-(N-(2,2-diphenylethyl carbamylmethyl)glycine 1-carboxy-1-(2,2-diphenyl-ethyl amino)cyclopropane | N-(N-(3,3-diphenylpropyl carbamylmethyl)glycine |

Although the proteinaceous molecules of the invention may inherently permeate membranes, membrane permeation may further be increased by the conjugation of a membrane permeating moiety to the proteinaceous molecule. Accordingly, in some embodiments the proteinaceous molecules of the invention comprise at least one membrane permeating moiety. The membrane permeating moiety may be conjugated at any point of the proteinaceous molecule. Suitable membrane permeating moieties include lipid moieties, cholesterol and proteins, such as cell-penetrating peptides and polycationic peptides; especially lipid moieties.

Suitable cell penetrating peptides may include the peptides described in, for example, US 20090047272, US 20150266935 and US 20130136742. Accordingly, suitable cell penetrating peptides may include, but are not limited to, basic poly(Arg) and poly(Lys) peptides and basic poly(Arg) and poly(Lys) peptides containing non-natural analogues of Arg and Lys residues such as YGRKKRPQRRR (HIV TAT47-57), RRWRRWWRRWWRRWRR (W/R), $CWK_{18}$ ($AlkCWK_{18}$), $K_{18}WCCWK_{18}$ ($Di$-$CWK_{18}$), WTLN-SAGYLLGKINLKALAALAKKIL (Transportan), GLFEA-LEELWEAK (DipaLytic), $K_{16}$GGCRGDMFGCAK$_{16}$RGD ($K_{16}$RGD), $K_{16}$GGCMFGCGG (P1), $K_{16}$ICRRARGDNPDDRCT (P2), KKWKMRRNQFWVK-VQRbAK (B) bA (P3), VAYISRGGVSTYYSDTVKGRF-TRQKYNKRA (P3a), IGRIDPANGKTKYAPKFQD-KATRSNYYGNSPS (P9.3), KETWWETWWTEWSQPKKKRKV (Pep-1), PLAEIDGI-ELTY (Plae), $K_{16}$GGPLAEIDGIELGA (Kplae), $K_{16}$GGPLAEIDGIELCA (cKplae), GALFLGFLG-GAAGSTMGAWSQPKSKRKV (MGP), WEAK(LAKA)$_2$-LAKH(LAKA)$_2$LKAC (HA2), (LARL)$_6$NHCH$_3$ (LARL$_6$), KLLKLLLKLWLLKLLL (Hel-11-7), (KKKK)$_2$GGC (KK), (KWKK)$_2$GCC (KWK), (RWRR)$_2$GGC (RWR), PKKKRKV (SV40 NLS7), PEVKKKRKPEYP (NLS12), TPPKKKRKVEDP (NLS12a), GGGGPKKKRK-VGG (SV40 NLS13), GGGFSTSLRARKA (AV NLS13), CKKKKKKSEDEYPYVPN (AV RME NLS 17), CKKKK-KKKSEDEYPYVPNFSTSLRARKA (AV FP NLS28), LVRKKRKTEEESPLKDKDAKKSKQE (SV40 N1 NLS24), and $K_9K_2K_4K_8GGK_5$ (Loligomer); HSV-1 tegument protein VP22; HSV-1 tegument protein VP22r fused with nuclear export signal (NES); mutant B-subunit of *Escherichia coli* enterotoxin EtxB (H57S); detoxified exotoxin A (ETA); the protein transduction domain of the HIV-1 Tat protein, GRKKRRQRRRPPQ; the *Drosophila melanogaster* Antennapedia domain Antp (amino acids 43-58), RQIKIWFQNRRMKWKK; Buforin II, TRSSRAGLQF-PVGRVHRLLRK; hClock-(amino acids 35-47) (human Clock protein DNA-binding peptide), KRVSRNKSEK-KRR; MAP (model amphipathic peptide), KLALKLALKA-LKAALKLA; K-FGF, AAVALLPAVLLALLAP; Ku70-derived peptide, comprising a peptide selected from the group comprising VPMLKE, VPMLK, PMLKE or PMLK; Prion, Mouse Prpe (amino acids 1-28), MANLGYWLLALFVT-MWTDVGLCKKRPKP; pVEC, LLIILRRRIRKQA-HAHSK; Pep-I, KETWWETWWTEWSQPKKKRKV; SynB1, RGGRLSYSRRRFSTSTGR; Transportan, GWTLNSAGYLLGKINLKALAALAKKIL; Transportan-10, AGYLLGKINLKALAALAKKIL; CADY, Ac-GL-WRALWRLLRSLWRLLWRA-cysteamide; Pep-7, SDL-WEMMMVSLACQY; HN-1, TSPLNIHNGQKL; VT5, DPKGDPKGVTVTVTVTVTGKGDPKPD; or pISL, RVIRVWFQNKRCKDKK.

In preferred embodiments, the membrane permeating moiety is a lipid moiety, such as a $C_{10}$-$C_{20}$ fatty acyl group, especially octadecanoyl (stearoyl; $C_{18}$), hexadecanoyl (palmitoyl; $C_{16}$) or tetradecanoyl (myristoyl; $C_{14}$); most especially tetradecanoyl. In preferred embodiments, the membrane permeating moiety is conjugated to the N- or C-terminal amino acid residue or through the amine of a lysine side-chain of the proteinaceous molecule, especially the N-terminal amino acid residue of the proteinaceous molecule. In particular embodiments, the membrane permeating moiety is conjugated through the amine of the N-terminal amino acid residue of the proteinaceous molecule.

For particular uses and methods of the invention, proteinaceous molecules with high levels of stability may be desired, for example, to increase the half-life of the proteinaceous molecule in a subject. Thus, in some embodiments, the proteinaceous molecules of the invention comprise a stabilizing moiety. The stabilizing moiety may be conjugated at any point on the proteinaceous molecule. Suitable stabilizing moieties include polyethylene glycol (PEG) or a capping moiety, including an acetyl group, pyroglutamate or an amino group. In preferred embodiments, the acetyl group and/or pyroglutamate are conjugated to the N-terminal amino acid residue of the proteinaceous molecule. In particular embodiments, the N-terminus of the proteinaceous molecule is a pyroglutamide or acetamide. In preferred embodiments, the amino group is conjugated to the C-terminal amino acid residue of the proteinaceous molecule. In particular embodiments, the proteinaceous molecule of the invention has a primary amide at the C-terminus. In preferred embodiments, the PEG is conjugated to the N-terminal or C-terminal amino acid residue of the proteinaceous molecule or through the amine of a lysine side-chain, especially through the N-terminal amino acid residue or through the amine of a lysine side-chain.

In preferred embodiments, the proteinaceous molecules of the invention have a primary amide or a free carboxyl group at the C-terminus and a primary amine at the N-terminus.

In some embodiments, the proteinaceous molecules of the present invention are cyclic peptides. Without wishing to be bound by theory, cyclization of peptides is thought to decrease the susceptibility of the peptides to degradation. In particular embodiments, the proteinaceous molecules are cyclized using N-to-C cyclization (head to tail cyclization), preferably through an amide bond. Such peptides do not possess N- or C-terminal amino acid residues. In particular embodiments, the proteinaceous molecules of the invention have an amide-cyclized peptide backbone. In other embodiments, the proteinaceous molecules of the invention are cyclized using side-chain to side-chain cyclization, preferably through a disulfide bond or a lactam bridge.

In some embodiments, the N- and C-termini are linked using a linking moiety. The linking moiety may be a peptide linker such that cyclization produces an amide-cyclized peptide backbone. Variation within the peptide sequence of the linking moiety is possible, such that the linking moiety may be modified to alter the physicochemical properties of the proteinaceous molecules and potentially reduce side effects of the proteinaceous molecules of the invention or otherwise improve the therapeutic use of the proteinaceous molecules, for example, by improving stability. The linking moiety will be of suitable length to span the distance between the N- and C-termini of the peptide without substantially altering the structural conformation of the proteinaceous molecule, for example, a peptidic linking moiety may be between 2 and 10 amino acid residues in length. In some embodiments, longer or shorter peptidic linking moieties may be required.

The proteinaceous molecules of the invention may be in the form of salts or prodrugs. The salts of the proteinaceous molecules of the present invention are preferably pharmaceutically acceptable, but it will be appreciated that non-pharmaceutically acceptable salts also fall within the scope of the present invention.

The proteinaceous molecules of the present invention may be in crystalline form and/or in the form of solvates, for example, hydrates. Solvation may be performed using methods known in the art.

In some embodiments, the proteinaceous molecules of the invention selectively inhibit PKC-θ over at least one other PKC enzyme or isoform, such as PKC-α, PKC-β, PKC-γ, PKC-δ, PKC-ε, PKC-ζ, PKC-η, PKC-λ, PKC-μ, or PKC-ν. In some embodiments, the proteinaceous molecules of the invention selectively inhibit PKC-θ over the other 10 PKC enzymes. In some embodiments, the proteinaceous molecules of the invention exhibit PKC-θ selectivity of greater than about 2-fold, 5-fold, 10-fold, 20-fold, 50-fold or greater than about 100-fold with respect to inhibition of one or more other PKC enzymes (i.e. one or more PKC enzymes other than PKC-θ, such as PKC-α, PKC-β, PKC-γ, PKC-δ, PKC-ε, PKC-ζ, PKC-η, PKC-λ, PKC-μ and/or PKC-ν). In other embodiments, selective molecules display at least 50-fold greater inhibition towards PKC-θ than towards one or more other PKC enzymes. In further embodiments, selective molecules display at least 100-fold greater inhibition towards PKC-θ than towards one or more other PKC enzymes. In still further embodiments, selective molecules display at least 500-fold greater inhibition towards PKC-θ than towards one or more other PKC enzymes. In yet further embodiments, selective molecules display at least 100-fold greater inhibition towards PKC-θ than towards one or more other PKC enzymes. In some embodiments, the proteinaceous molecules of the invention are non-selective PKC-θ inhibitors.

The present invention also contemplates nucleic acid molecules which encode a proteinaceous molecule of the invention. Thus, in a further aspect of the present invention, there is provided an isolated nucleic acid molecule comprising a polynucleotide sequence that encodes a proteinaceous molecule of the invention or is complementary to a polynucleotide sequence that encodes a proteinaceous molecule of the invention, such as the proteinaceous molecule of Formula I, SEQ ID NO: 1 or 2 or variant proteinaceous molecule as described herein.

In some embodiments, the proteinaceous molecule encoded by the polynucleotide sequence is other than a proteinaceous molecule consisting of the amino acid sequence of SEQ ID NO: 1.

The isolated nucleic acid molecules of the present invention may be DNA or RNA. When the nucleic acid is in DNA form, it may be genomic DNA or cDNA. RNA forms of the nucleic acid molecules of the present invention are generally mRNA.

Although the nucleic acid molecules are typically isolated, in some embodiments the nucleic acid molecules may be integrated into, ligated to, or otherwise fused or associated with other genetic molecules, such as an expression vector. Generally an expression vector includes transcriptional and translational regulatory nucleic acid operably linked to the polynucleotide sequence. Accordingly, in another aspect of the invention, there is provided an expression vector comprising a polynucleotide sequence that encodes a proteinaceous molecule of the invention, such as the proteinaceous molecule of Formula I, SEQ ID NO: 1 or 2 or variant proteinaceous molecule as described herein.

In some embodiments, the proteinaceous molecules of the invention may be produced inside a cell by introduction of one or more expression constructs, such as an expression vector, that comprise a polynucleotide sequence that encodes a proteinaceous molecule of the invention.

The invention contemplates recombinantly producing the proteinaceous molecules of the invention inside a host cell, such as a mammalian cell (e.g. Chinese hamster ovary (CHO) cell, mouse myeloma (NSO) cell, baby hamster kidney (BHK) cell or human embryonic kidney (HEK293) cell), yeast cell (e.g. *Pichia pastoris* cell, *Saccharomyces cerevisiae* cell, *Schizosaccharomyces pombe* cell, *Hansenula polymorpha* cell, *Kluyveromyces lactis* cell, *Yarrowia lipolytica* cell or *Arxula adeninivorans* cell), or bacterial cell (e.g. *Escherichia coli* cell, *Corynebacterium glutamicum* or *Pseudomonas fluorescens* cell).

For therapeutic applications, the invention also contemplates producing the proteinaceous molecules of the invention in vivo inside a PKC-θ overexpressing cell, such as a vertebrate cell, particularly a mammalian or avian cell, especially a mammalian cell.

As described, for example, in U.S. Pat. No. 5,976,567, the expression of natural or synthetic nucleic acids is typically achieved by operably linking a polynucleotide sequence encoding a proteinaceous molecule of the invention to a regulatory element (e.g. a promoter, which may be either constitutive or inducible), suitably incorporating the construct into an expression vector and introducing the vector into a suitable host cell. Typical vectors contain transcription and translation terminators, transcription and translation initiation sequences and promoters useful for regulation of the expression of the nucleic acid. The vectors optionally comprise generic expression cassettes containing at least one independent terminator sequence, sequences permitting replication of the cassette in eukaryotes, prokaryotes or both, (e.g. shuttle vectors) and selection markers for both prokaryotic and eukaryotic systems. Vectors may be suitable for replication and integration in prokaryotes, eukaryotes, or both. See, Giliman and Smith (1979), *Gene*, 8: 81-97; Roberts et al. (1987) *Nature*, 328: 731-734; Berger and Kimmel, Guide to Molecular Cloning Techniques, Methods in Enzymology, volume 152, Academic Press, Inc., San Diego, Calif. (Berger); Sambrook et al. (1989), Molecular Cloning—a Laboratory Manual (2nd ed.) Vol. 1-3, Cold Spring Harbor Laboratory, Cold Spring Harbor Press, N.Y.; and Ausubel et al., (1994) Current Protocols in Molecular Biology, eds., Current Protocols, a joint venture between Greene Publishing Associates, Inc. and John Wiley & Sons, Inc. (Supplement).

Expression vectors containing regulatory elements from eukaryotic viruses such as retroviruses are typically used for expression of nucleic acid sequences in eukaryotic cells. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

While a variety of vectors may be used, it should be noted that viral expression vectors are useful for modifying eukaryotic cells because of the high efficiency with which the viral vectors transfect target cells and integrate into the target cell genome. Illustrative expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000) *Curr. Opin. Biotechnol.*, 11(2): 205-208; Vigna and Naldini (2000) *J. Gene Med*, 2(5): 308-316; Kay et al. (2001) *Nat. Med.*, 7(1): 33-40; Athanasopoulos et al. (2000) *Int. J. Mol. Med*, 6(4): 363-375; and Walther and Stein (2000) *Drugs*, 60(2): 249-271.

The polypeptide or peptide-encoding portion of the expression vector may comprise a naturally-occurring sequence or a variant thereof, which has been engineered using recombinant techniques. In one example of a variant, the codon composition of a polynucleotide encoding a proteinaceous molecule of the invention is modified to permit enhanced expression of the proteinaceous molecule of the invention in a mammalian host using methods that take advantage of codon usage bias, or codon translational efficiency in specific mammalian cell or tissue types as set forth, for example, in International Publications WO 99/02694 and WO 00/42215. Briefly, these latter methods are based on the observation that translational efficiencies of different codons vary between different cells or tissues and that these differences can be exploited, together with codon composition of a gene, to regulate expression of a protein in a particular cell or tissue type. Thus, for the construction of codon-optimized polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5%, 10%, 15%, 20%, 25%, 30%, more preferably 35%, 40%, 50%, 60%, 70% or more of the existing codons of a parent polynucleotide.

The expression vector is compatible with the cell in which it is introduced such that the proteinaceous molecule of the invention is expressible by the cell. The expression vector is introduced into the cell by any suitable means which will be dependent on the particular choice of expression vector and cell employed. Such means of introduction are well-known to those skilled in the art. For example, introduction can be effected by use of contacting (e.g. in the case of viral vectors), electroporation, transformation, transduction, conjugation or triparental mating, transfection, infection membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art. Alternatively, the vectors are introduced by means of cationic lipids, e.g., liposomes. Such liposomes are commercially available (e.g., Lipofectin®, Lipofectamine™, and the like, supplied by Life Technologies, Gibco BRL, Gaithersburg, Md.).

The proteinaceous molecules of the present invention may be prepared using recombinant DNA techniques or by chemical synthesis.

In some embodiments, the proteinaceous molecules of the present invention are prepared using standard peptide synthesis methods, such as solution synthesis or solid phase synthesis. The chemical synthesis of the proteinaceous molecules of the invention may be performed manually or using an automated synthesizer. For example, the linear peptides may be synthesized using solid phase peptide synthesis using either Boc or Fmoc chemistry, as described in Merrifield (1963) *J Am Chem Soc*, 85(14): 2149-2154; Schnolzer, et al. (1992) *Int J Pept Protein Res*, 40: 180-193; Ensenat-Waser, et al. (2002) *IUBMB Life*, 54:33-36; WO 2002/010193 and Cardosa, et al. (2015) *Mol Pharmacol*, 88(2): 291-303. Following deprotection and cleavage from the solid support, the linear peptides are purified using suitable methods, such as preparative chromatography.

In other embodiments, the proteinaceous molecules of the invention may be cyclized. Cyclization may be performed using several techniques, for example, as described in Davies (2003) *J Pept Sci*, 9: 471-501.

In some embodiments, the proteinaceous molecules of the present invention are prepared using recombinant DNA techniques. For example, the proteinaceous molecules of the invention may be prepared by a procedure including the steps of: (a) preparing a construct comprising a polynucleotide sequence that encodes the proteinaceous molecule of the invention and that is operably linked to a regulatory element; (b) introducing the construct into a host cell; (c) culturing the host cell to express the polynucleotide sequence to thereby produce the encoded proteinaceous molecule of the invention; and (d) isolating the proteinaceous molecule of the invention from the host cell. The proteinaceous molecule of the present invention may be prepared recombinantly using standard protocols, for example, as described in Klint, et al. (2013) *PLOS One*, 8(5): e63865; Sambrook, et al. (1989) Molecular Cloning: A Laboratory Manual (Cold Spring Harbour Press), in particular Sections 16 and 17; Ausubel, et al. (1998) Current Protocols in Molecular Biology (John Wiley and Sons, Inc.), in particular Chapters 10 and 16; and Coligan, et al. (1997) Current Protocols in Protein Science (John Wiley and Sons, Inc.), in particular Chapters 1, 5 and 6.

3. Pharmaceutical Compositions

In accordance with the present invention, the proteinaceous molecules are useful in compositions and methods for the treatment or prevention of a condition involving PKC-θ overexpression, such as a cancer.

Thus, in some embodiments, the proteinaceous molecule of the present invention may be in the form of a pharmaceutical composition, wherein the pharmaceutical composition comprises a proteinaceous molecule of the invention and a pharmaceutically acceptable carrier or diluent.

The proteinaceous molecules of the invention may be formulated into the pharmaceutical compositions as neutral or salt forms.

As will be appreciated by those skilled in the art, the choice of pharmaceutically acceptable carrier or diluent will be dependent on the route of administration and on the nature of the condition and the subject to be treated. The particular carrier or delivery system and route of administration may be readily determined by a person skilled in the art. The carrier or delivery system and route of administration should be carefully selected to ensure that the activity of the proteinaceous molecule is not depleted during preparation of the formulation and the proteinaceous molecule is able to reach the site of action intact. The pharmaceutical compositions of the invention may be administered through a variety of routes including, but not limited to, oral, rectal, topical, intranasal, intraocular, transmucosal, intestinal, enteral, intramuscular, subcutaneous, intramedullary, intrathecal, intraventricular, intracerebral, intravaginal, intravesical, intravenous or intraperitoneal administration.

The pharmaceutical forms suitable for injectable use include sterile injectable solutions or dispersions and sterile powders for the preparation of sterile injectable solutions. Such forms should be stable under the conditions of manufacture and storage and may be preserved against reduction, oxidation and microbial contamination.

A person skilled in the art will readily be able to determine appropriate formulations for the proteinaceous molecules of the invention using conventional approaches. Techniques for formulation and administration may be found in, for example, Remington (1980) Remington's Pharmaceutical Sciences, Mack Publishing Co., Easton, Pa., latest edition.

Identification of preferred pH ranges and suitable excipients, such as antioxidants, is routine in the art, for example, as described in Katdare and Chaubel (2006) Excipient Development for Pharmaceutical, Biotechnology and Drug Delivery Systems (CRC Press). Buffer systems are routinely used to provide pH values of a desired range and may include, but are not limited to, carboxylic acid buffers, such as acetate, citrate, lactate, tartrate and succinate; glycine; histidine; phosphate; tris(hydroxymethyl)aminomethane (Tris); arginine; sodium hydroxide; glutamate; and carbonate buffers. Suitable antioxidants may include, but are not limited to, phenolic compounds such as butylated hydroxytoluene (BHT) and butylated hydroxyanisole; vitamin E; ascorbic acid; reducing agents such as methionine or sulphite; metal chelators such as ethylene diamine tetraacetic acid (EDTA); cysteine hydrochloride; sodium bisulfite; sodium metabisulfite; sodium sulphite; ascorbyl palmitate; lecithin; propyl gallate; and alpha-tocopherol.

For injection, the proteinaceous molecules of the invention may be formulated in aqueous solutions, suitably in physiologically compatible buffers such as Hanks' solution, Ringer's solution or physiological saline buffer. For transmucosal administration, penetrants appropriate to the barrier to be permeated are used in the formulation. Such penetrants are generally known in the art.

The compositions of the present invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives and hydrophilic beeswax derivatives.

Alternatively, the proteinaceous molecules of the present invention can be formulated readily using pharmaceutically acceptable carriers well known in the art into dosages suitable for oral administration, which is also contemplated for the practice of the present invention. Such carriers enable the bioactive agents of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulfate, vegetable oils, synthetic oils, polyols, alginic acid, phosphate buffered solutions, emulsifiers, isotonic saline and pyrogen-free water.

Pharmaceutical formulations for parenteral administration include aqueous solutions of the proteinaceous molecules of the invention in water-soluble form. Additionally, suspensions of the proteinaceous molecules of the invention may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances that increase the viscosity of the suspension, such as sodium carboxymethyl cellulose, sorbitol or dextran. Optionally, the suspension may also contain suitable stabilizers or agents that increase the solubility of the compounds to allow for the preparation of highly concentrated solutions.

Sterile solutions may be prepared by combining the active compounds in the required amount in the appropriate solvent with other excipients as described above as required, followed by sterilization, such as filtration. Generally, dispersions are prepared by incorporating the various sterilized active compounds into a sterile vehicle which contains the basic dispersion medium and the required excipients as described above. Sterile dry powders may be prepared by vacuum- or freeze-drying a sterile solution comprising the active compounds and other required excipients as described above.

Pharmaceutical preparations for oral use can be obtained by combining the proteinaceous molecules of the invention with solid excipients and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g. by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of particle doses.

Pharmaceuticals which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The proteinaceous molecules of the invention may be incorporated into modified-release preparations and formulations, for example, polymeric microsphere formulations, and oil- or gel-based formulations.

In particular embodiments, the proteinaceous molecule of the invention may be administered in a local rather than systemic manner, such as by injection of the proteinaceous molecule directly into a tissue, which is preferably subcutaneous or omental tissue, often in a depot or sustained release formulation.

Furthermore, the proteinaceous molecule of the invention may be administered in a targeted drug delivery system, such as in a particle which is suitable targeted to and taken up selectively by a cell or tissue. In some embodiments, the proteinaceous molecule of the invention is contained or otherwise associated with a vehicle selected from liposomes, micelles, dendrimers, biodegradable particles, artificial DNA nanostructure, lipid-based nanoparticles and carbon or old nanoparticles. In illustrative examples of this type, the vehicle is selected from poly(lactic acid) (PLA), poly(glycolic acid) (PGA), poly(lactic-co-glycolic acid) (PLGA), poly(ethylene glycol) (PEG), PLA-PEG copolymers and combinations thereof.

In cases of local administration or selective uptake, the effective local concentration of the agent may not be related to plasma concentration.

It is advantageous to formulate the compositions in dosage unit form for ease of administration and uniformity of dosage. The determination of the novel dosage unit forms of the present invention is dictated by and directly dependent on the unique characteristics of the active material, the particular therapeutic effect to be achieved and the limitations inherent in the art of compounding active materials for the treatment of disease in living subjects having a diseased condition in which bodily health is impaired as herein disclosed in detail.

While the proteinaceous molecule of the invention may be the sole active ingredient administered to the subject, the administration of other cancer therapies concurrently with said proteinaceous molecule is within the scope of the invention. For example, the proteinaceous molecule of Formula I, SEQ ID NO: 1 or 2 or variant described herein may be administered concurrently with one or more cancer therapies, non-limiting examples of which include radiotherapy, surgery, chemotherapy, hormone ablation therapy, pro-apoptosis therapy and immunotherapy; particularly chemotherapy. The proteinaceous molecule of the invention may be therapeutically used before treatment with the cancer therapy, may be therapeutically used after the cancer therapy or may be therapeutically used together with the cancer therapy.

Suitable radiotherapies include radiation and waves that induce DNA damage, for example, $\gamma$-irradiation, X-rays, UV irradiation, microwaves, electronic emissions and radioisotopes. Typically, therapy may be achieved by irradiating the localized tumor site with the above described forms of radiations. It is most likely that all of these factors cause a broad range of damage to DNA, on the precursors of DNA, on the replication and repair of DNA and on the assembly and maintenance of chromosomes.

The dosage range for X-rays ranges from daily doses of 50-200 roentgens for prolonged periods of time such as 3-4 weeks, to single doses of 2000-6000 roentgens. Dosage ranges for radioisotopes vary widely and depend on the half life of the isotope, the strength and type of radiation emitted and the uptake by the neoplastic cells. Suitable radiotherapies may include, but are not limited to, conformal external beam radiotherapy (50-100 Gray given as fractions over 4-8 weeks), either single shot or fractionated high dose brachytherapy, permanent interstitial brachytherapy and systemic radioisotopes such as Strontium 89. In some embodiments, the radiotherapy may be administered with a radiosensitizing agent. Suitable radiosensitizing agents may include, but are not limited to, efaproxiral, etanidazole, fluosol, misonidazole, nimorazole, temoporfin and tirapazamine.

Suitable chemotherapeutic agents may include, but are not limited to, antiproliferative/antineoplastic drugs and combinations thereof including alkylating agents (for example cisplatin, carboplatin, cyclophosphamide, nitrogen mustard, melphalan, chlorambucil, busulphan and nitrosoureas), antimetabolites (for example antifolates such as fluoropyridines like 5-fluorouracil and tegafur, raltitrexed, methotrexate, cytosine arabinoside and hydroxyurea), antitumor antibiotics (for example anthracyclines like adriamycin, bleomycin, doxorubicin, daunomycin, epirubicin, idarubicin, mitomycin-C, dactinomycin and mithramycin), antimitotic agents (for example *Vinca* alkaloids like vincristine, vinblastine, vindesine and vinorelbine and taxoids like paclitaxel and docetaxel), and topoisomerase inhibitors (for example epipodophyllotoxins like etoposide and teniposide, amsacrine, topotecan and camptothecin); cytostatic agents such as antiestrogens (for example tamoxifen, toremifene, raloxifene, droloxifene and idoxifene), estrogen receptor down regulators (for example fulvestrant), antiandrogens (for example bicalutamide, flutamide, nilutamide and cyproterone acetate), UH antagonists or LHRH agonists (for example goserelin, leuprorelin and buserelin), progestogens (for example megestrol acetate), aromatase inhibitors (for example as anastrozole, letrozole, vorozole and exemestane) and inhibitors of 5α-reductase such as finasteride; agents which inhibit cancer cell invasion (for example metalloproteinase inhibitors like marimastat and inhibitors of urokinase plasminogen activator receptor function); inhibitors of growth factor function, for example such inhibitors include growth factor antibodies, growth factor receptor antibodies (for example the anti-erbb2 antibody trastuzumab [Herceptin™] and the anti-erbb1 antibody Cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (Gefitinib, AZD1839), N-(3-ethynylphenyl)-6,7-bis(2-methoxyethoxy) quinazolin-4-amine (Erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family; antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin); vascular damaging agents such as Combretastatin A4 and compounds disclosed in International Patent Applications WO 99/02166, WO00/40529, WO 00/41669, WO01/92224, WO02/04434 and WO02/08213; antisense therapies, for example those which are directed to the targets listed above, such as ISIS 2503, an anti-ras antisense; and gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Suitable immunotherapy approaches may include, but are not limited to ex vivo and in vivo approaches to increase the immunogenicity of patient tumor cells such as transfection with cytokines including interleukin 2, interleukin 4 or granulocyte-macrophage colony stimulating factor; approaches to decrease T-cell anergy; approaches using transfected immune cells such as cytokine-transfected dendritic cells; approaches using cytokine-transfected tumor cell lines; and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

Examples of other cancer therapies include phytotherapy, cryotherapy, toxin therapy or pro-apoptosis therapy. A person skilled in the art would appreciate that this list is not exhaustive of the types of treatment modalities available for cancer and other hyperplastic lesions.

It is well known that chemotherapy and radiation therapy target rapidly dividing cells and/or disrupt the cell cycle or cell division. These treatments are offered as part of the treating several forms of cancer, aiming either at slowing their progression or reversing the symptoms of disease by means of a curative treatment. However, these cancer treatments may lead to an immunocompromised state and ensuing pathogenic infections and, thus, the present invention also extends to combination therapies, which employ a proteinaceous molecule of Formula I, SEQ ID NO: 1 or 2 or variant described herein, a cancer therapy and an anti-infective agent that is effective against an infection that develops or that has an increased risk of developing from an immunocompromised condition resulting from the cancer therapy. The anti-infective drug is suitably selected from antimicrobials, which may include, but are not limited to, compounds that kill or inhibit the growth of microorganisms such as viruses, bacteria, yeast, fungi, protozoa, etc. and, thus, include antibiotics, amebicides, antifungals, antiprotozoals, antimalarials, antituberculotics and antivirals. Antiinfective drugs also include within their scope anthelmintics and nematocides. Illustrative antibiotics include quinolones (e.g. amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin;

and garenoxacin), tetracyclines, glycylcyclines and oxazolidinones (e.g. chlortetracycline, demeclocycline, doxycycline, lymecycline, methacycline, minocycline, oxytetracycline, tetracycline, tigecycline; linezolide, eperezolid), glycopeptides, aminoglycosides (e.g. amikacin, arbekacin, butirosin, dibekacin, fortimicins, gentamicin, kanamycin, menomycin, netilmicin, ribostamycin, sisomicin, spectinomycin, streptomycin, tobramycin), β-lactams (e.g. imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephacetrile, cephalexin, cephaloglycin, cephaloridine, cephalothin, cephapirin, cephradine, cefinetazole, cefoxitin, cefotetan, azthreonam, carumonam, flomoxef, moxalactam, amdinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g. azithromycin, clarithromycin, erythromycin, oleandomycin, rokitamycin, rosaramicin, roxithromycin, troleandomycin), ketolides (e.g. telithromycin, cethromycin), coumermycins, lincosamides (e.g. clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir and zidovudine.

Suitable amebicides or antiprotozoals include, but are not limited to, atovaquone, chloroquine hydrochloride, chloroquine phosphate, metronidazole, metronidazole hydrochloride and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin and terbinafine hydrochloride. Suitable antimalarials include, but are not limited to, chloroquine hydrochloride, chloroquine phosphate, doxycycline, hydroxychloroquine sulfate, mefloquine hydrochloride, primaquine phosphate, pyrimethamine and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine and streptomycin sulfate.

As previously described, the proteinaceous molecule may be compounded for convenient and effective administration in effective amounts with a suitable pharmaceutically acceptable carrier in dosage unit form. In some embodiments, a unit dosage form may comprise the active peptide of the invention in amount in the range of from about 0.25 µg to about 2000 mg. The active peptide of the invention may be present in an amount of from about 0.25 µg to about 2000 mg/mL of carrier. In embodiments where the pharmaceutical composition comprises one or more additional active ingredients, the dosages are determined by reference to the usual dose and manner of administration of the said ingredients.

4. Methods

In accordance with the present invention, the proteinaceous molecules of the invention are useful in methods for altering at least one of formation, proliferation, maintenance, EMT or MET of a PKC-θ overexpressing cell. The proteinaceous molecules of the invention are useful for the treatment or prevention of a condition involving PKC-θ overexpression in a subject, such as a cancer.

Accordingly, in another aspect of the present invention, there is provided the use of the isolated or purified proteinaceous molecule of the invention, particularly the proteinaceous molecule of Formula I, SEQ ID NO: 1 or 2 or variant peptide described herein, for therapy.

In yet another aspect of the present invention, there is provided the use of the isolated or purified proteinaceous molecule of the invention, particularly the proteinaceous molecule of Formula I, SEQ ID NO: 1 or 2 or variant peptide described herein, in the manufacture of a medicament for therapy.

In still another aspect of the present invention, there is provided an isolated or purified proteinaceous molecule of the invention, particularly the proteinaceous molecule of Formula I, SEQ ID NO: 1 or 2 or variant peptide described herein, for use in therapy.

In yet another aspect of the invention, there is provided a method of inhibiting or reducing the nuclear translocation of PKC-θ in a PKC-θ overexpressing cell, comprising contacting the PKC-θ overexpressing cell with a proteinaceous molecule of the invention, particularly the proteinaceous molecule of Formula I, SEQ ID NO: 1 or 2 or variant peptide described herein.

The present invention also provides the use of a proteinaceous molecule of the invention, particularly the proteinaceous molecule of Formula I, SEQ ID NO: 1 or 2 or variant peptide described herein, for inhibiting or reducing the nuclear translocation of PKC-θ in a PKC-θ overexpressing cell.

There are numerous conditions involving PKC-θ overexpression in which the proteinaceous molecules of the invention may be useful. Accordingly, in a further aspect of the invention, there is provided a method of treating or preventing a condition in a subject in respect of which PKC-θ inhibition is associated with effective treatment, comprising administering to the subject a proteinaceous molecule of the invention, particularly the proteinaceous molecule of Formula I, SEQ ID NO: 1 or 2 or variant peptide described herein.

The present invention also contemplates the use of a proteinaceous molecule of the invention, particularly the proteinaceous molecule of Formula I, SEQ ID NO: 1 or 2 or variant peptide described herein, in the manufacture of a medicament for treating or preventing a condition in a subject in respect of which PKC-θ inhibition is associated with effective treatment.

In a still further aspect of the present invention, there is provided the use of a proteinaceous molecule of the invention, particularly the proteinaceous molecule of Formula I, SEQ ID NO: 1 or 2 or variant peptide described herein, for treating or preventing a condition in a subject in respect of which PKC-θ inhibition is associated with effective treatment.

In another aspect of the present invention, there is provided a proteinaceous molecule of the invention, particularly the proteinaceous molecule of Formula I, SEQ ID NO: 1 or 2 or variant peptide described herein, for use in treating or preventing a condition in a subject in respect of which PKC-θ inhibition is associated with effective treatment.

Conditions involving PKC-θ overexpression may include, but are not limited to, cancer; neurological and vascular disorders such as Down's syndrome, memory and cognitive impairment, dementia, amyloid neuropathies, brain inflammation, nerve and brain trauma, vascular amyloidosis, depression or cerebral hemorrhage with amyloidosis; acute and chronic airway disorders such as bronchitis, obstructive bronchitis, spastic bronchitis, allergic bronchitis, allergic asthma, bronchial asthma, emphysema or chronic obstructive pulmonary disease (COPD); dermatoses such as psoriasis, toxic and allergic contact eczema, atopic eczema, seborrheic eczema, lichen simplex, sunburn, pruritis in the anogenital area, alopecia areata, hypertrophic scars, discoid lupus erythematosus, follicular and wide-area pyodermias, endogenous and exogenous acne or acne rosacea; arthritic conditions such as rheumatoid arthritis, rheumatoid spondylitis, osteoarthritis or other arthritic conditions; acquired immunodeficiency syndrome (AIDS); multiple sclerosis; human immunodeficiency virus (HIV) infection; septic shock; adult respiratory distress syndrome; graft-versus-host reactions; acute or chronic rejection of organ or tissue allografts or xenografts; Crohn's disease; ulcerative colitis; inflammatory bowel disease; allergic rhinitis or sinitis; allergic conjunctivitis; nasal polyps autoimmune disorders; or diabetes insipidus.

In yet another aspect of the present invention, there is provided, a method of altering at least one of (i) formation; (ii) proliferation; (iii) maintenance; (iv) epithelial to mesenchymal cell transition; or (v) mesenchymal to epithelial cell transition of a PKC-θ overexpressing cell, comprising contacting said PKC-θ overexpressing cell with an isolated or purified proteinaceous molecule of the invention, particularly the proteinaceous molecule of Formula I, SEQ ID NO: 1 or 2 or variant peptide described herein.

In still another aspect of the invention, there is provided the use of an isolated or purified proteinaceous molecule of the invention, particularly the proteinaceous molecule represented by Formula I or the proteinaceous molecule comprising, consisting or consisting essentially of the amino acid sequence of SEQ ID NO: 1, 2 or variant proteinaceous molecule described herein, in the manufacture of a medicament for altering at least one of (i) formation; (ii) proliferation; (iii) maintenance; (iv) epithelial to mesenchymal cell transition; or (v) mesenchymal to epithelial cell transition of a PKC-θ overexpressing cell.

In yet another aspect of the invention, there is provided the isolated or purified proteinaceous molecule of the invention, particularly the proteinaceous molecule of Formula I, SEQ ID NO: 1 or 2 or variant peptide described herein, for use in altering at least one of (i) formation; (ii) proliferation; (iii) maintenance; (iv) epithelial to mesenchymal cell transition; or (v) mesenchymal to epithelial cell transition of a PKC-θ overexpressing cell.

In some embodiments, the proteinaceous molecule of the invention results in a reduction, impairment, abrogation or prevention of the (i) formation; (ii) proliferation; (iii) maintenance; or (iv) EMT of a PKC-θ overexpressing cell; and/or in the enhancement of (v) MET of a PKC-θ overexpressing cell.

In a further aspect of the invention, there is provided the use of an isolated or purified proteinaceous molecule of the invention, particularly the proteinaceous molecule represented by Formula I or the proteinaceous molecule comprising, consisting or consisting essentially of the amino acid sequence of SEQ ID NO: 1, 2 or variant proteinaceous molecule described herein, in the manufacture of a medicament for reducing, impairing, abrogating or preventing the (i) formation; (ii) proliferation; (iii) maintenance; or (iv) EMT of a PKC-θ overexpressing cell; and/or enhancing (v) MET of a PKC-θ overexpressing cell.

Suitable PKC-θ overexpressing cells may include, but are not limited to, breast, prostate, lung, bladder, pancreatic, colon, melanoma, liver or glioma cells; especially breast cells. In particular embodiments, the PKC-θ overexpressing cell is a breast epithelial cell, especially a breast ductal epithelial cell.

In particular embodiments, the PKC-θ overexpressing cell is a CSC or a non-CSC tumor cell; preferably a CSC tumor cell. In some embodiments, the CSC tumor cell expresses CD24 and CD44, particularly $CD44^{high}$, $CD24^{low}$.

In yet another aspect of the invention, there is provided a method of treating or preventing a cancer in a subject, wherein the cancer comprises at least one PKC-θ overexpressing cell, comprising administering to the subject an isolated or purified proteinaceous molecule of the invention, particularly the proteinaceous molecule represented by Formula I, or the proteinaceous molecule comprising, consisting or consisting essentially of the amino acid sequence of SEQ ID NO: 1, 2 or variant proteinaceous molecule described herein.

In some embodiments, the proteinaceous molecules of the invention are used for treating, preventing and/or relieving the symptoms of a malignancy, particularly a metastatic cancer. In preferred embodiments, the proteinaceous molecules of the invention are used for treating, preventing and/or relieving the symptoms of a metastatic cancer.

In a still further aspect of the invention, there is provided the use of an isolated or purified proteinaceous molecule of the invention, particularly the proteinaceous molecule represented by Formula I or the proteinaceous molecule comprising, consisting or consisting essentially of the amino acid sequence of SEQ ID NO: 1, 2 or variant proteinaceous molecule described herein, in the manufacture of a medicament for treating or preventing a cancer in a subject, wherein the cancer comprises at least one PKC-θ overexpressing cell.

In another aspect of the invention, there is provided an isolated or purified proteinaceous molecule of the invention, particularly the proteinaceous molecule of Formula I, SEQ ID NO: 1 or 2 or variant peptide described herein, for use in treating or preventing a cancer in a subject, wherein the cancer comprises at least one PKC-θ overexpressing cell.

The present invention also contemplates the use of an isolated or purified proteinaceous molecule of the invention, particularly the proteinaceous molecule of Formula I, SEQ ID NO: 1 or 2 or variant peptide described herein, for treating or preventing a cancer in a subject, wherein the cancer comprises at least one PKC-θ overexpressing cell.

The proteinaceous molecules of the invention are suitable for treating an individual who has been diagnosed with a cancer, who is suspected of having a cancer, who is known to be susceptible and who is considered likely to develop a cancer, or who is considered likely to develop a recurrence of a previously treated cancer. The cancer may be hormone receptor positive or hormone receptor negative. In some embodiments, the cancer is hormone receptor negative and is, thus, resistant to hormone or endocrine therapy. In some embodiments where the cancer is breast cancer, the breast cancer is hormone receptor negative. In some embodiments, the breast cancer is estrogen receptor negative and/or progesterone receptor negative.

In particular embodiments, the methods and uses involve the administration of one or more further active agents as described in Section 3 supra, such as an additional cancer therapy and/or anti-infective agent; particularly a cancer therapy; especially a chemotherapeutic. The one or more further active agents and proteinaceous molecule may be administered separately, simultaneously or sequentially.

A skilled person would be well aware of suitable assays used to evaluate PKC-θ inhibition, such as inhibition of nuclear translocation, and to identify proteinaceous molecules that are PKC-θ inhibitors, for example, the assays described in Sutcliffe, et al. (2012) Front Immunol, 3: 260; Ghildyal, et al. (2009) J Virol, 83(11): 5353-5362; Riss T L, et al. (2013) Cell Viability Assays, In: Sittampalam, et al., Assay Guidance Manual [Internet]. Bethesda (Md.): Eli Lilly & Company and the National Center for Advancing Translational Sciences, available from: http://www.ncbi.nlm.nih.gov/books/NBK144065/; US 2005222186; Li, et al. (2011) J Biomol Screen, 16(2): 141-154; and Zhang, et al. (2010) FEBS Letters, 584(22): 4646-4654.

EXAMPLES

Certain embodiments of the invention will now be described with reference to the following examples, which are intended for the purpose of illustration only and are not intended to limit the scope of the generality hereinbefore described.

All materials and reagents used in the synthesis and testing of the peptides are commercially available, for example, from Sigma-Aldrich Co., Novabiochem, Abcam and American Type Culture Collection (ATCC) unless otherwise stated.

Example 1 Synthesis of Importinib Peptides

Importinib4759 and importinib4759_O1 (Table 4) were synthesized using automated modern solid phase peptide synthesis and purification technology using the mild Fmoc chemistry method, for example, as described in Ensenat-Waser, et al. (2002) IUBMB Life, 54:33-36 and WO 2002/010193. Peptides were purified using automated preparative reversed phase-high performance liquid chromatography (RP-HPLC). Fractions were analyzed using analytical RP-HPLC and mass spectrometry. Fractions of 98% purity or higher were combined to give the final product.

TABLE 4

Importinib peptide sequences

| Name | SEQ ID NO | Amino Acid Sequence |
|---|---|---|
| Importinib4759 | 1 | RKEIDPPFRPKVK-OH |
| Importinib4759_O1 | 2 | RRKRIDWPPRRKPK-OH |

All peptides tested in the in vitro tests were myristoylated through the N-terminal amino group of the N-terminal amino acid. Myristoylation was carried out by covalently coupling myristic acid to the N-terminal residue using standard N,N'-diisopropylcarbodiimide (DIC)/hydroxybenzotriazole (HOBt) coupling as described above, prior to deprotection and purification of the peptides.

All testing described in the following examples was performed using N-myristoylated peptides.

Example 2 Importinib Peptides Specifically Block Nuclear PKC-θ Translocation without Affecting Other PKC Isomers and Importins MCF7 cells were pre-seeded overnight on sterile coverslips in 12 well plates with 1 mL of completed Dulbecco's modified eagle medium (DMEM) before incubating with 50 µM of importinib4759 (synthesized in accordance with Example 1) and importinib4759_O1 (synthesized in accordance with Example 1) for 24 hr. Test peptides were not removed when MCF7 cells were stimulated with 0.65 ng/mL of phorbol 12-myristate 13-acetate (PMA) for 60 hr. Diethylpyrocarbonate (DEPC)-water was used for control (test peptides were dissolved in sterile DEPC-water). After wash with Dulbecco's phosphate buffered saline (DPBS) twice, samples on coverslips were fixed with 4% paraformaldehyde for 10 minutes and stained with PKC-θ (Cat. SC-212), PKC-θ-Phosphor-T538, PKC-β2, PKC-α, Importin α, or Importin 8 primary Antibody respectively and conjugated Alexa-488 secondary Antibody. Cell nucleus was stained with anti-fade 2-(4-amidinophenyl)-6-indolecarbamidine dihydrochloride (DAPI). When samples were dried overnight, Nikon fluorescence microscopy was used to take photos. ImageJ software was used for densimetric analysis. Fn/c was calculated using the formula: Fn/c=(nuclear density-background density)/(cytoplasmic density-background density).

Importinib4759 and importinib4759_O1 are capable of blocking nuclear PKC-θ (FIGS. 1a and 1b; $p<0.0001$ relative to control). However, importinib4759_O1 has significantly higher capacity to prevent PKC-θ nuclear translocation compared to importinib4759. Importinib4759_O1 had no effect on the distribution of other PKC isoforms such as PKC-α and PKC-β2 (FIG. 1c), as well as import proteins such as Importin α and Importin 8 (FIG. 1d) (p=not significant relative to control).

Example 3 Importinib Peptides Inhibit $CD44^{hi}CD24^{lo}$ Cancer Stem Cell Formation in MCF-IM Model $5\times10^4$ MCF7 cells were seeded with 1 mL of complete DMEM in 12 well plates overnight, then importinib4759 (5004 and 100 µM; synthesized in accordance with Example 1) or importinib4759_O1 (2504 and 50 µM; synthesized in accordance with Example 1) were used to treat cells for 24 hr before stimulation with PMA for 60 hr. Samples were harvested by trypsinization followed by washing with DPBS containing 2% heat inactivated foetal bovine serum (HI-FBS). FACS staining were performed using anti-human CD44-APC, anti-human CD24-PE, Hoechst, and anti-human EpCAM antibody cocktails. Data was collected from BD FACSLSR-II flow cytometer. Treestar FlowJo was used for data analysis.

Figure 2:
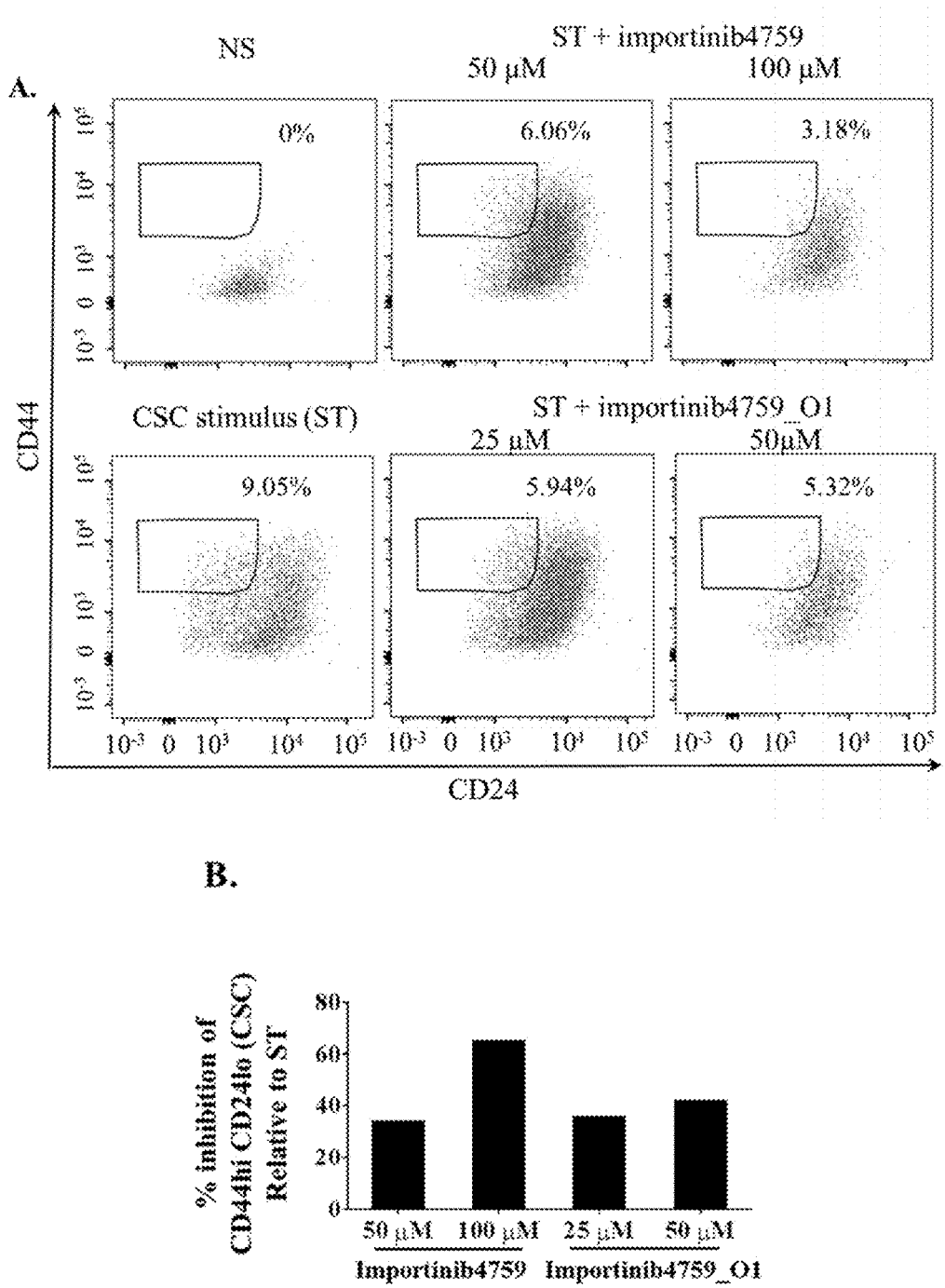
FIG. 2 Effect of importinib peptides on CD44$^{hi}$CD24$^{lo}$ cancer stem cell formation in MCF-IM model. (A) Representation of FACS plots of MCF-IM cells after importinib peptide treatment, which are gated from forward scatter and side scatter, followed by Hoechst negative population (live cells); (B) Percentage of CD44$^{hi}$CD24$^{lo}$ (CSC) inhibition by importinib peptides relative to control ST (stimulated) samples (importinib4759 and importinib4759_O1 have a p-value of 0.0079 relative to ST).

Cancer stem cell formation was inhibited by both importinib4759 and importinib4759_O1 (FIGS. 2a and 2b; p=0.0079 relative to control).

Example 4 Importinib Peptides Reduce $CD44^{hi}CD24^{lo}$ Cancer Stem Cell Formation in MDA-MB-231 Model $5\times10^4$ MDA-MB-231 cells were seeded with 1 mL of complete DMEM in 12 well plates overnight, then importinib4759 (5004 and 100 μM; synthesized in accordance with Example 1) or importinib4759_O1 (2504 and 50 μM; synthesized in accordance with Example 1) were used to treat cells for 48 hr before samples were harvested by trypsinization followed by washing with DPBS containing 2% HI-FBS. FACS staining was performed using anti-human CD44-APC, anti-human CD24-PE, Hoechst, and anti-human EpCAM antibody cocktails. Data was collected from BD FACSLSR-II flow cytometer. Treestar FlowJo was used for data analysis.

Figure 3:
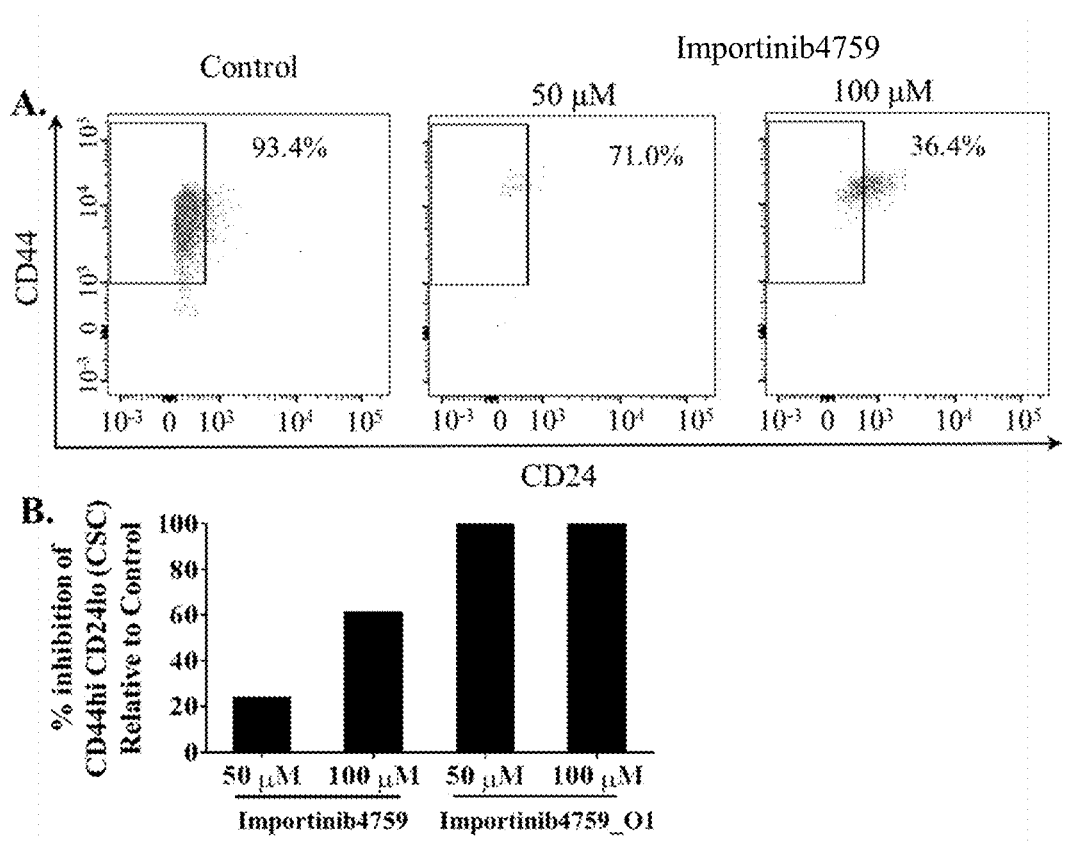
FIG. 3 Effect of importinib peptides on CD44$^{hi}$CD24$^{lo}$ cancer stem cell formation in MDA-MB-231 model. (A) Representation of FACS plots of MDA-MB-231 cells after importinib4759 treatment, which are gated from forward scatter and side scatter, followed by Hoechst negative population (live cells); (B) Percentage of CD44$^{hi}$CD24$^{lo}$ (CSC) inhibition by importinib peptides relative to control ST (stimulated) samples (importinib4759 and importinib4759_O1 have a p-value of <0.0001 relative to ST); (C) Representation of live cell population after importinib4759_O1 treatment in MCF7 or MDA-MB-231 cells.
Figure 3:
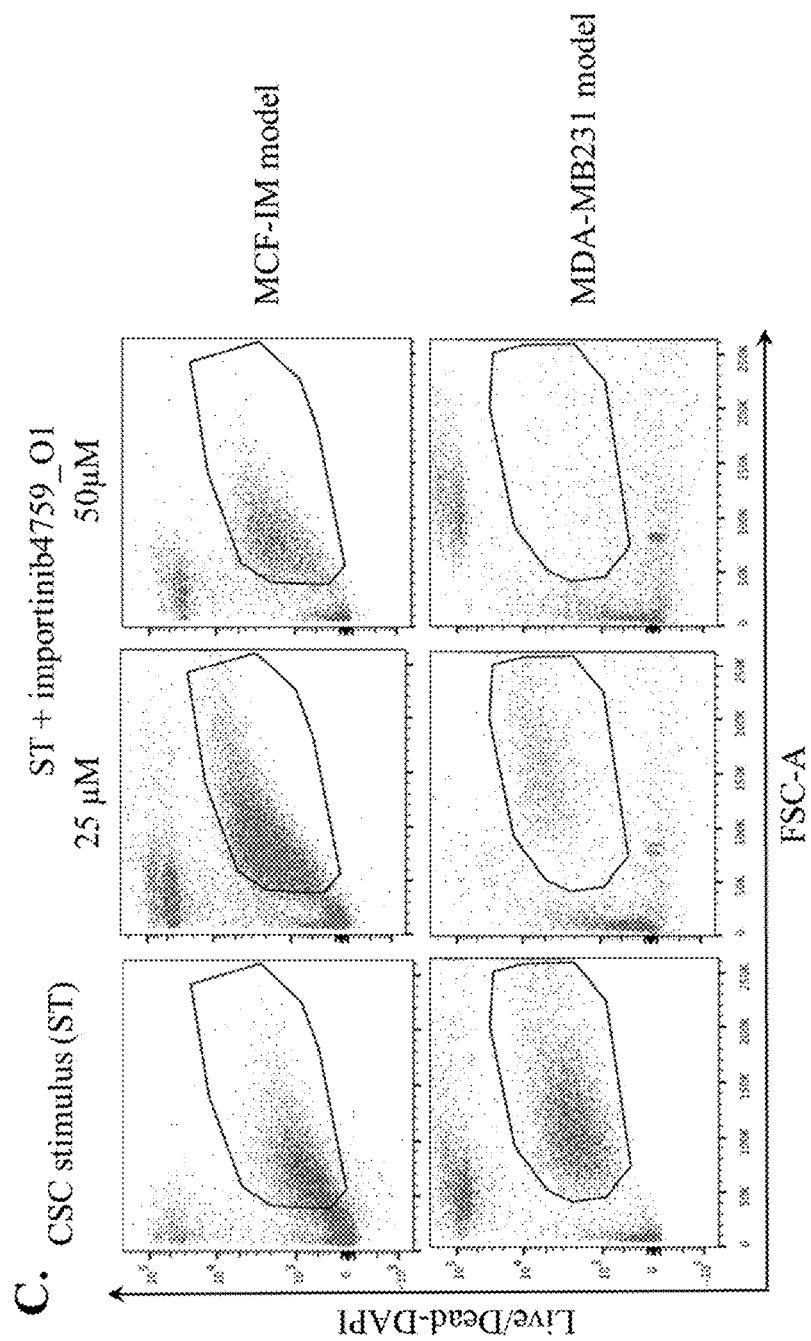

Significant reduction of cancer stem cells was detected following treatment with 50 μM or 10004 importinib4759 (FIGS. 3a and 3b; p=<0.0001 relative to control). Importinib4759_O1 cleared virtually all MDA-MB-231 cells, while the same concentration of inhibitor had minimal effect on MCF7 epithelial cells (FIGS. 3b and 3c; p<0.0001 relative to control).

Example 5 Importinib4759_O1 Significantly Blocks Nuclear Translocation of Transcription Factors NF-κB p65 and p53 and Enhances Tumor Suppressor Proteins Such as Rb MCF7 cells were pre-seeded overnight on sterile coverslips in 12 well plates with 1 mL of completed DMEM before inhibiting with 50 μM of importinib4759_O1 (synthesized in accordance with Example 1) for 24 hr. Importinib4759_O1 was removed when MCF7 cells were stimulated with 0.65 ng/mL of PMA for 60 hr. DEPC-water was used as the control (importinib4759_O1 was dissolved in sterile DEPC-water). After washing with DPBS twice, samples on coverslips were fixed with 4% paraformaldehyde for 10 minutes and stained with p65, Rb, or p53 primary Antibody and conjugated Alexa-488 secondary Antibody. Cell nucleus was stained with anti-fade DAPI. When samples were dried overnight, Nikon fluorescence microscopy was used to take photos. ImageJ software was used for densimetric analysis. Fn/c was calculated using the formula: Fn/c=(nuclear density-background density)/(cytoplasmic density-background density).

Figure 4:
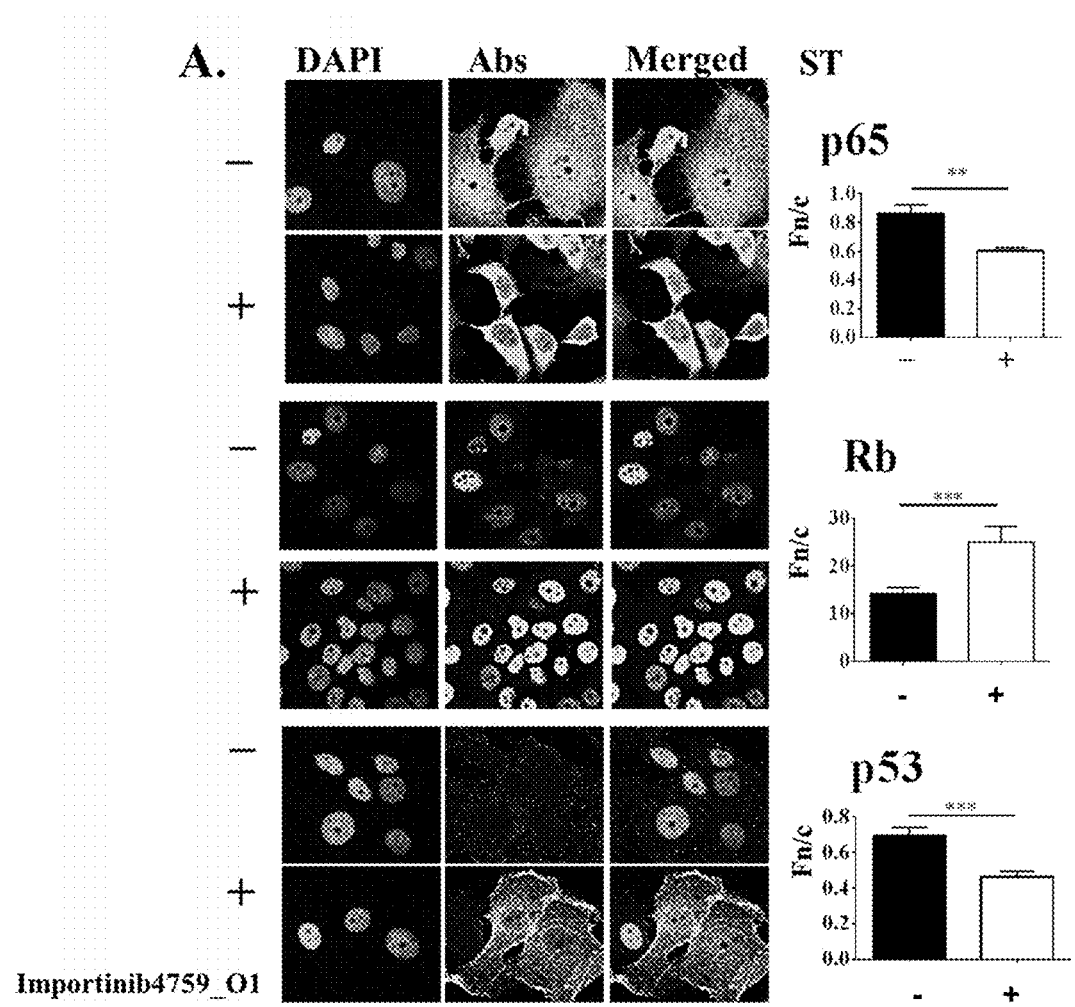
FIG. 4 Effect of importinib4759_O1 on nuclear translocation of transcription factors NF-κB p65 and p53, and tumor suppressor proteins such as Rb. (A) Representation of immunofluorescence microscopy pictures and the plot of Fn/c for MCF7 cells treated with importinib4759_O1. – represents stimulated control; + represents stimulated samples pre-treated with importinib4759_O1. Importinib4759_O1 has a p-value of 0.0033 in relation to p65, a p-value of 0.0007 in relation to Rb, and a p-value of 0.0009 in relation to p53 relative to control. **=p-value of ≤0.0001; *=p-value of ≤0.001; **=p-value of ≤0.01; *=p-value of ≤0.05; ns=p-value of ≥0.05.

Importinib4759_O1 significantly inhibited nuclear expression of NF-κB transcription factors p65 and p53 (FIG. 4; p=0.0033 and 0.0009, respectively). Importinib4759_O1 enhanced expression of the tumor suppressor protein Rb (FIG. 4; p=0.0007).

Example 6 Peptide Inhibitors Targeting Other PKC Isoforms had No Effect on Nuclear Transportation of PKC-9 nPKC-β1, nPKC-ε and nPKC-δ peptide inhibitors were designed based on the nuclear localization signal of PKC-β1, PKC-ε and PKC-δ respectively. The sequences of these peptides are presented in Table 5. These peptides were synthesized and N-myristoylated using the method of Example 1.

TABLE 5

| Peptide inhibitor sequences | |
|---|---|
| Peptide Inhibitor | Amino Acid Sequence |
| nPKC-β1 | RKEIQPPYKPKAR |
| nPKC-ε | KKIKPPFKPRIKTKR |
| nPKC-δ | KRRLEPPFRPKVK |

Figure 5:
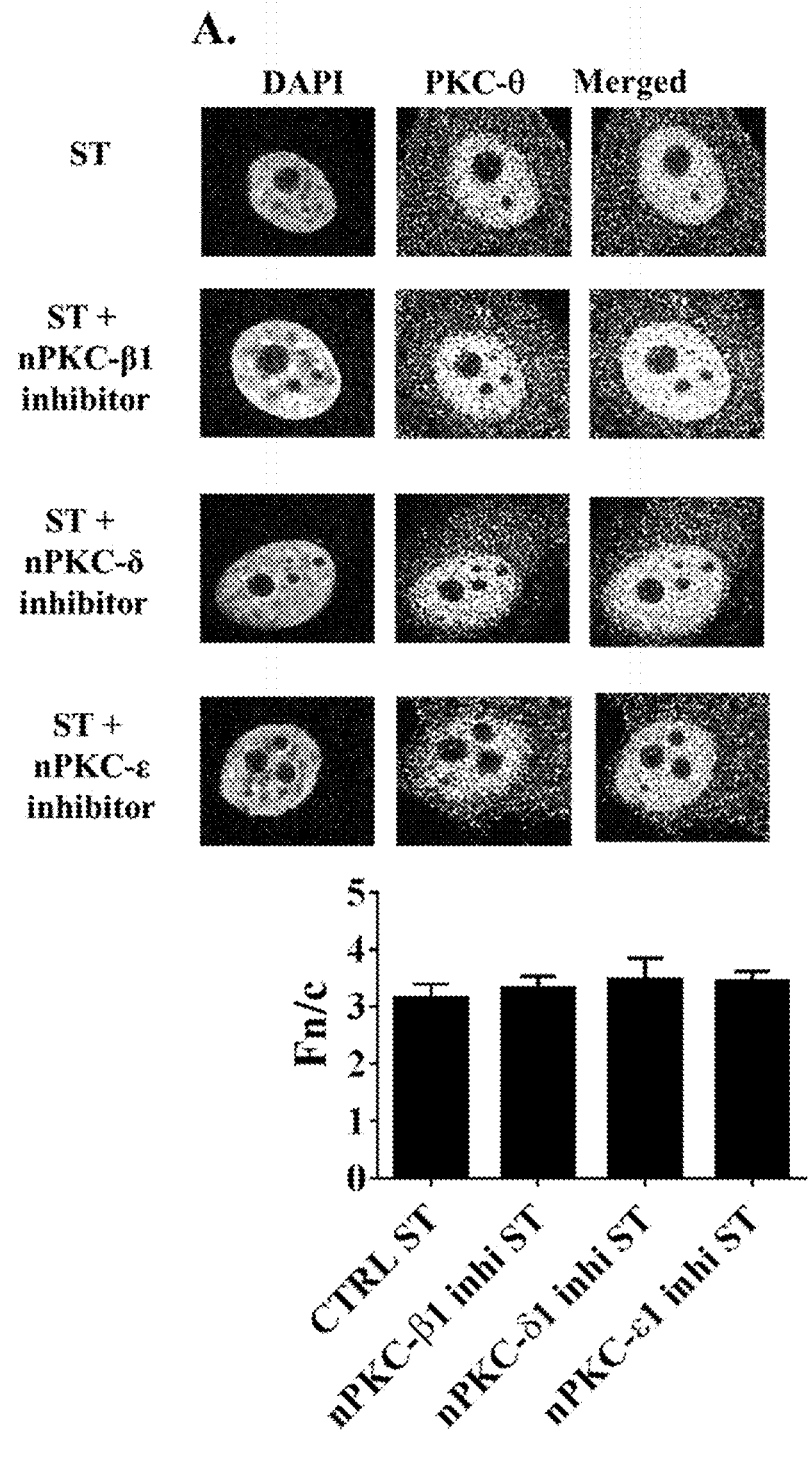
FIG. 5 Effect of peptide inhibitors targeting other PKC isoforms on nuclear transportation of PKC-θ. (A) Representation of immunofluorescence microscopy pictures and the plot of Fn/c for cells treated with peptide inhibitors targeting PKC-β1, PKC-θ and PKC-ε, where ST represents stimulated samples.

MCF7 cells were pre-seeded overnight on sterile coverslips in 12 well plates with 1 mL of completed DMEM before inhibiting with 50 μM of nPKC-β1, nPKC-ε or nPKC-δ peptide inhibitor respectively for 24 hr. Inhibitors were not removed when MCF7 cells were stimulated with 0.65 ng/mL of PMA for 60 hr. DEPC-water was used for control (test peptides were dissolved in sterile DEPC-water). After washing with DPBS twice, samples on coverslips were fixed with 4% paraformaldehyde for 10 minutes and stained with PKC-θ-phosphor-T538 primary Antibody and conjugated Alexa-488 secondary Antibody. Cell nucleus was stained with anti-fade DAPI. When samples were dried overnight, Nikon fluorescence microscopy was used to take photos. ImageJ software was used for densimetric analysis. Fn/c was calculated using the formula: Fn/c=(nuclear density-background density)/(cytoplasmic density-background density).

nPKC-β1, nPKC-δ or nPKC-ε peptide inhibitors had no effect on the nuclear localization of PKC-θ (FIG. 5).

Example 7 Effect of Importinib Peptides on a Balb/c-Nude MDA-MB-231 Xenograft Breast Cancer Model A Balb/c-nude MDA-MB-231 xenograft breast cancer model was utilized to determine the effect of the importinib peptides alone and in combination with the chemotherapeutic, docetaxel in comparison to a randomized peptide control.

Five week old balb/c-nude mice (n=5 per test compound) were injected with MDA-MB-231 human breast carcinoma cell suspensions (2×106 cells in 25 μL PBS mixed with 25 μL of BD Matrigel Matrix) subcutaneously into the right mammary gland. Test compounds in a saline vehicle [4 mg/kg docetaxel; 8 mg/kg, 40 mg/kg and 60 mg/kg importinib4759 or importinib4759_O1 (synthesized in accordance with Example 1); 4 mg/kg docetaxel with 8 mg/kg importinib4759 or importinib4759_O1; 4 mg/kg docetaxel with 40 mg/kg importinib4759 or importinib4759_O1; 4 mg/kg docetaxel with 60 mg/kg importinib4759 or importinib4759_O1; or randomized peptide control] were injected intraperitoneally. Tumor volume was assessed using calipers daily over a period of five weeks following treatment. Animals were sacrificed after the five week period. Tumor grafts were removed using resection and processed into single cell suspensions. The percentage of cancer stem cells was determined using FACS analysis. FACS staining was performed using anti-human CD44-APC, anti-human CD24-PE, Hoechst, and anti-human EpCAM antibody cocktails. Data was collected from BD FACSLSR-II flow cytometer. Treestar FlowJo was used for data analysis. Significance was determined using a one-way ANOVA or Mann-Whitney T-test.

Figure 6:
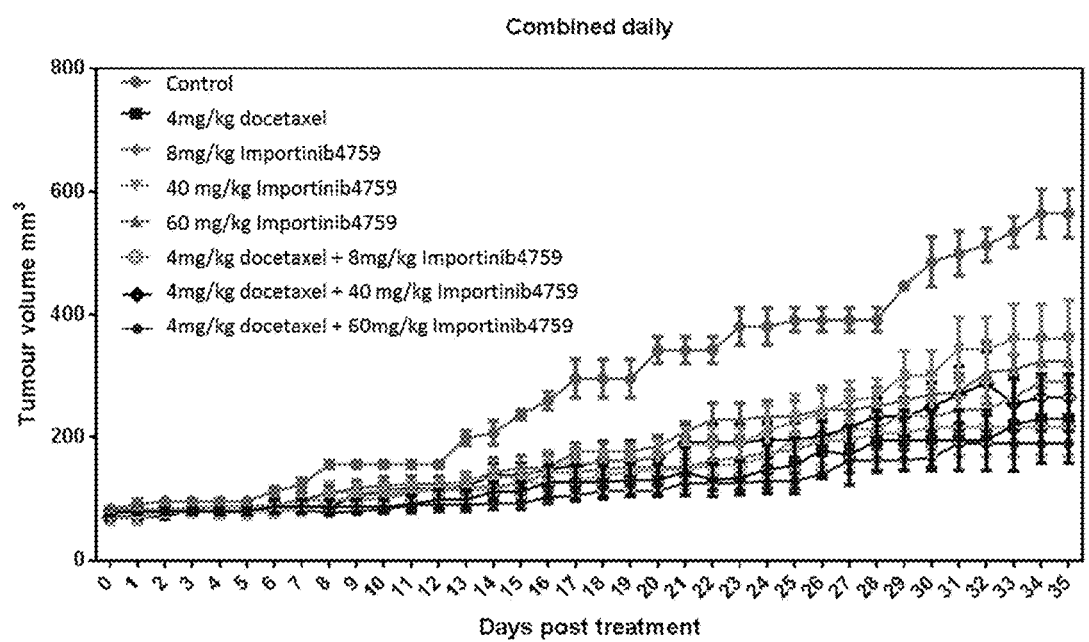
FIG. 6 Line graph over time showing the effect of importinib4759 and docetaxel on tumor volume in a Balb/c-nude MDA-MB-231 xenograft breast cancer model (data shown as mean±SE). Importinib4759 has an overall p-value of 0.003.
Figure 7:
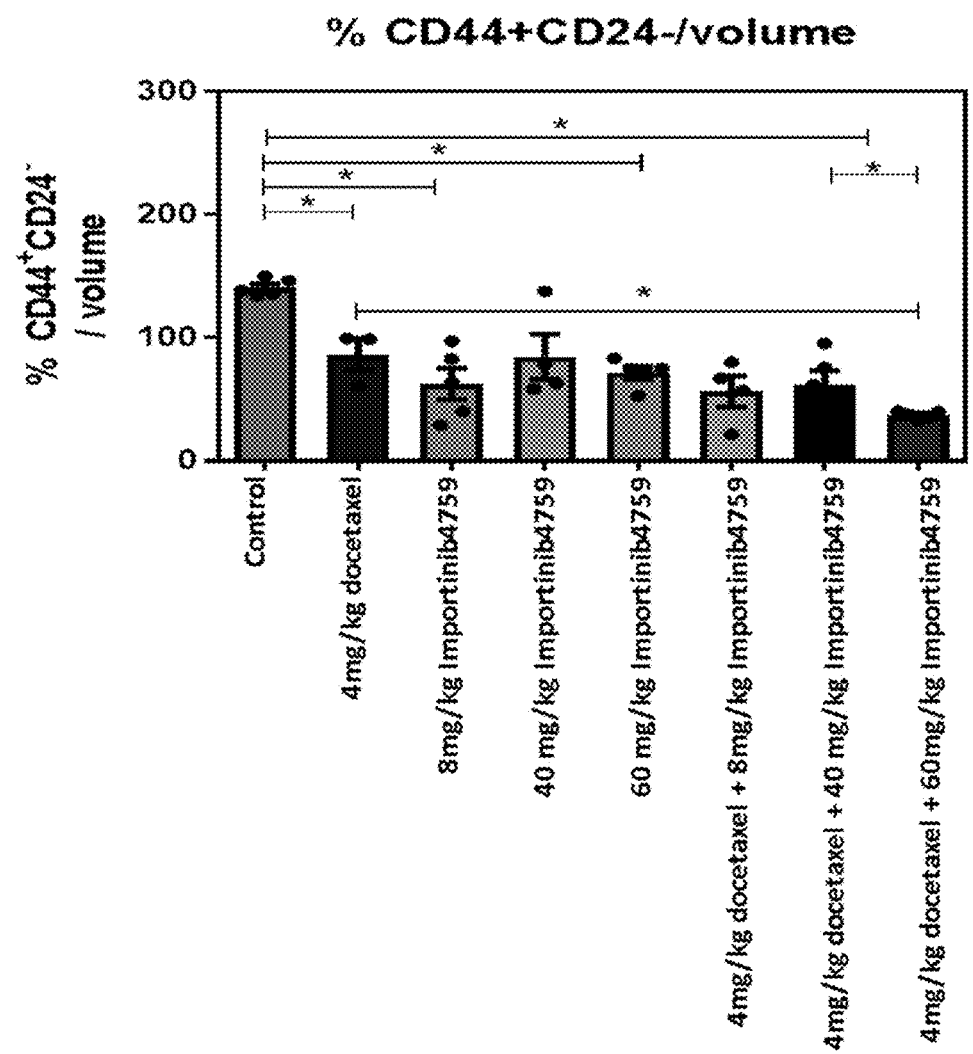
FIG. 7 Bar graph showing the effect of importinib4759 and docetaxel on cancer stem cell (CD44$^{high}$CD24$^{low}$) proportion in a Balb/c-nude MDA-MB-231 xenograft breast cancer model (data shown as mean±SE). Importinib4759 has an overall p-value of 0.0317.

The administration of importinib4759 significantly reduced tumor volume over time (FIG. 6; overall p=0.003). However, the combination of importinib4759 and docetaxel caused a marked reduction in tumor volume, with both the combination treatment and importinib4759 treatment abrogating tumor volume in comparison to the control or docetaxel treatment alone. Importinib4759 had a preference for cancer stem cells ($CD44^{high}CD24^{low}$), with both importinib4759 treatment alone and in combination with docetaxel significantly abrogating the cancer stem cell population (FIG. 7; overall p=0.0317).

Figure 8:
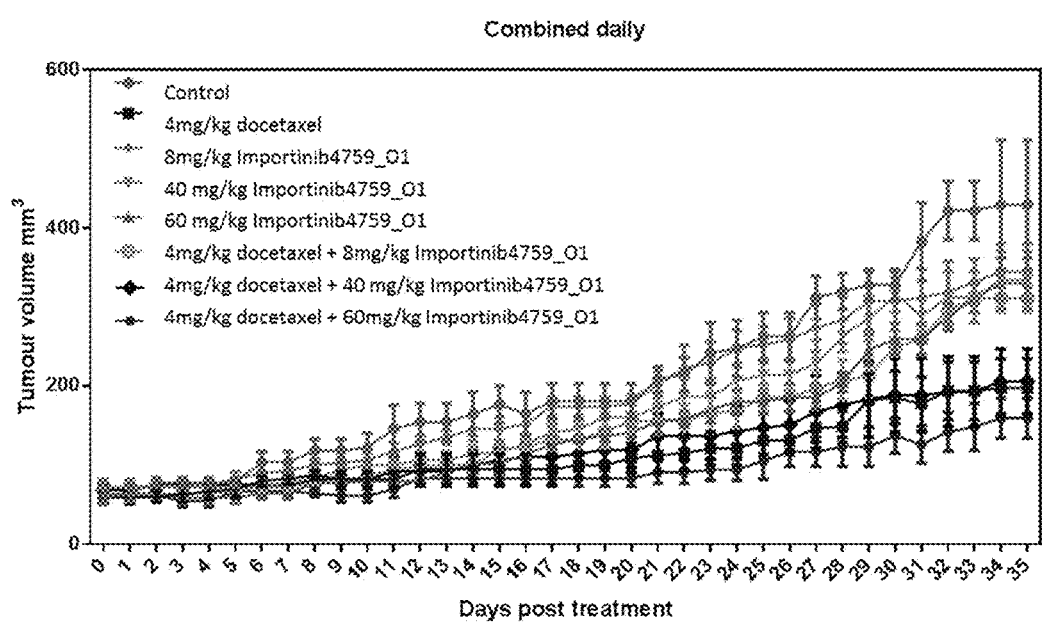
FIG. 8 Line graph over time showing the effect of importinib4759_O1 and docetaxel on tumor volume in a Balb/c-nude MDA-MB-231 xenograft breast cancer model (data shown as mean±SE). Importinib4759_O1 has an overall p-value of 0.0079.
Figure 9:
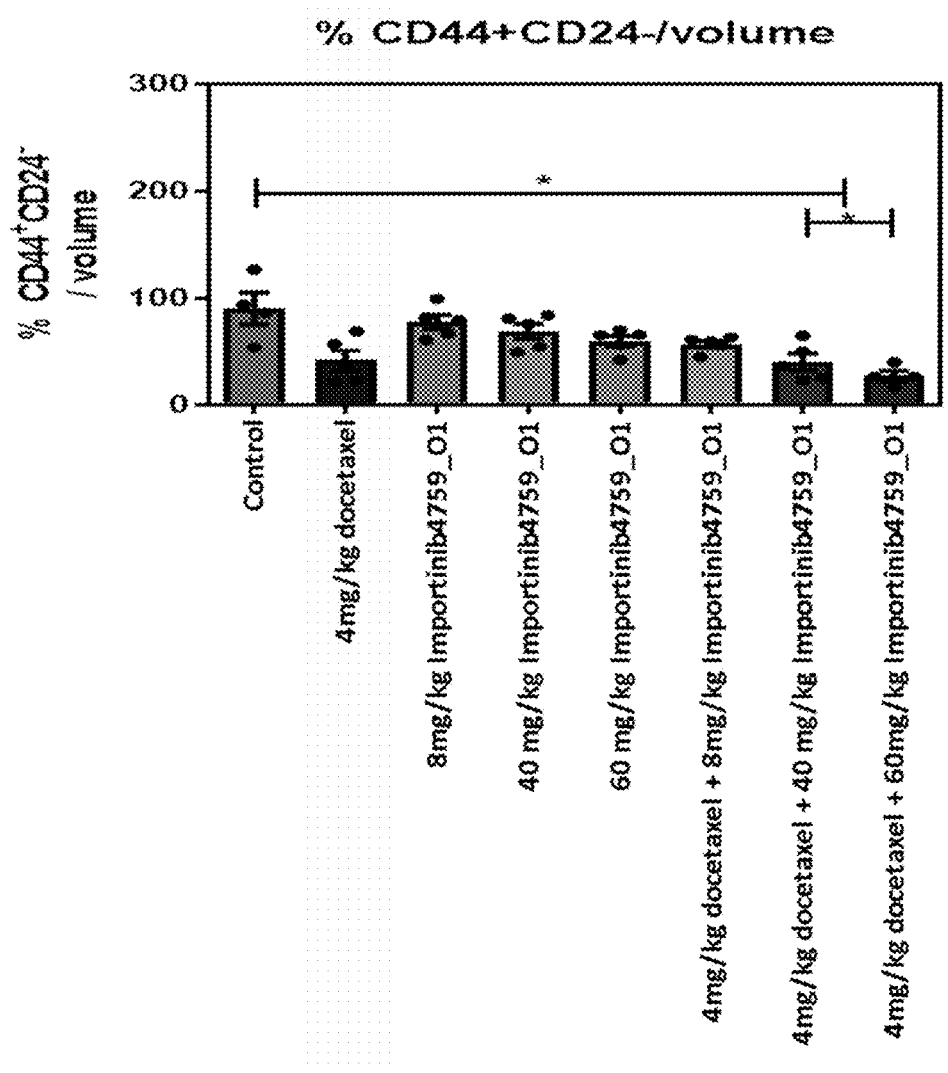
FIG. 9 Bar graph showing the effect of importinib4759_O1 and docetaxel on cancer stem cell (CD44$^{high}$CD24$^{low}$) proportion in a Balb/c-nude MDA-MB-231 xenograft breast cancer model (data shown as mean±SE). Importinib4759_O1 has an overall p-value of 0.0286.
Figure 10:
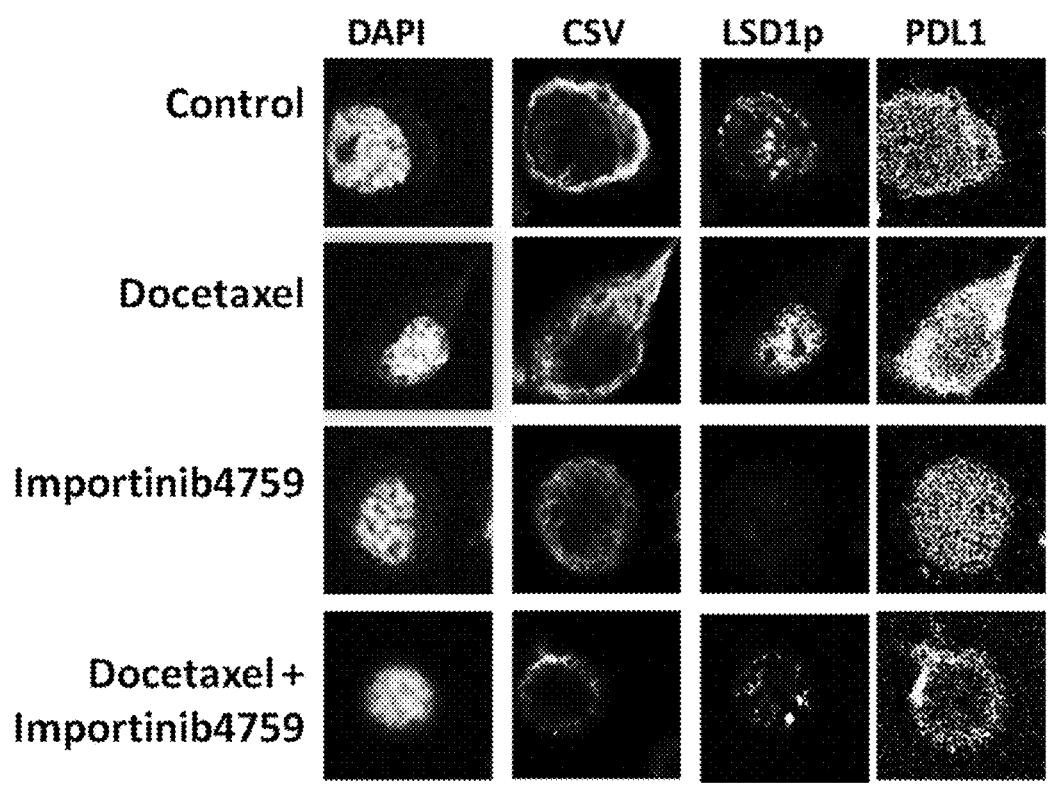
FIG. 10 Representation of confocal microscopy pictures showing the effect of importinib4759 and docetaxel on expression of cancer stem cell markers (CSV, LSD1p and PDL1) in cells derived from a Balb/c-nude MDA-MB-231 xenograft breast cancer model.
Figure 11:
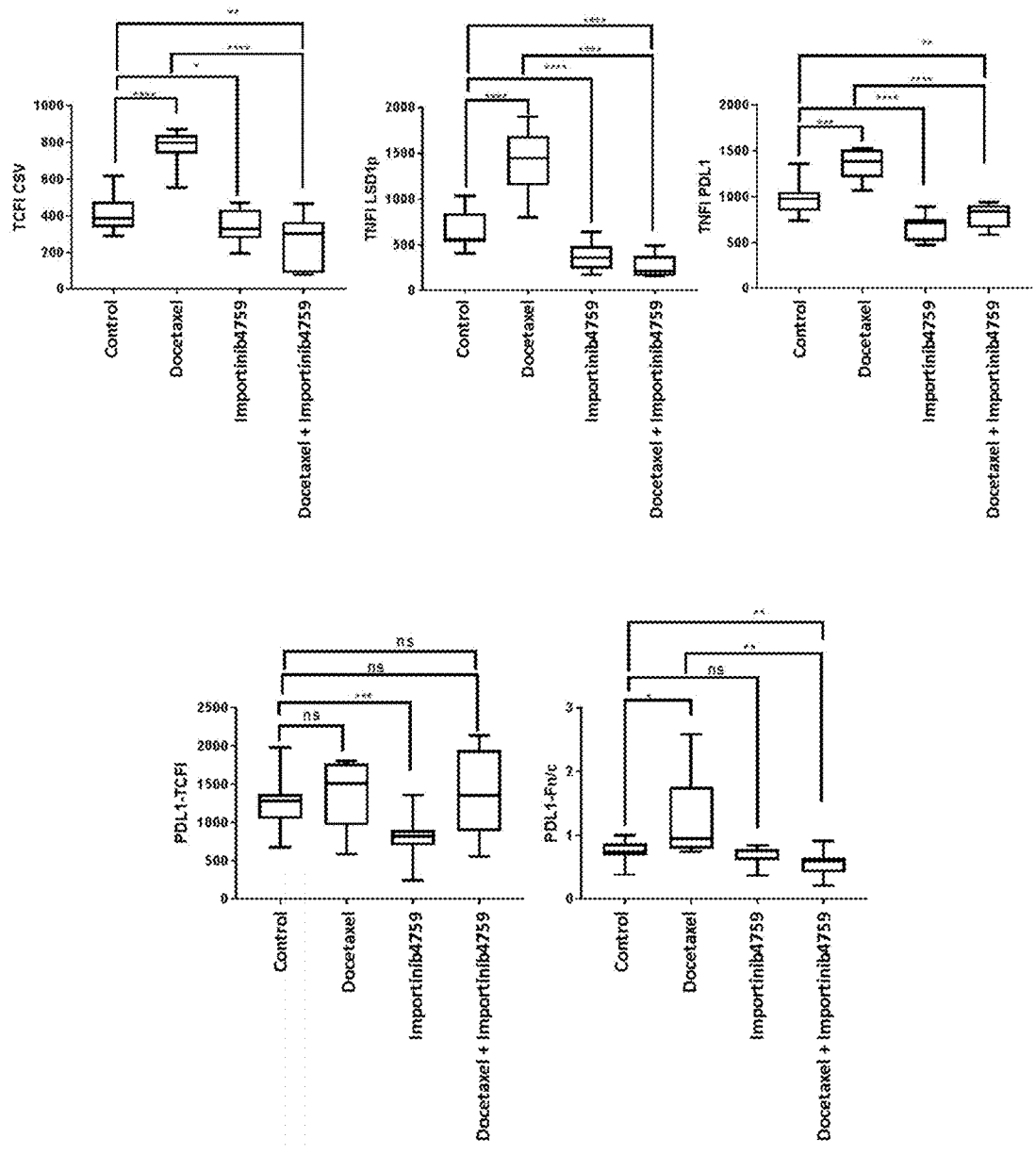
FIG. 11 Graphs presenting the effect of importinib4759 and docetaxel on nuclear (TNFI) and cytoplasmic (TCFI) expression of cancer stem cell markers (CSV, LSD1p and PDL1) in cells derived from a Balb/c-nude MDA-MB-231 xenograft breast cancer model (n≥20 individual cells; data shown as mean±SE). **=p-value of ≤0.0001; *=p-value of ≤0.001; **=p-value of ≤0.01; *=p-value of ≤0.05; ns=p-value of ≥0.05.
Figure 12:
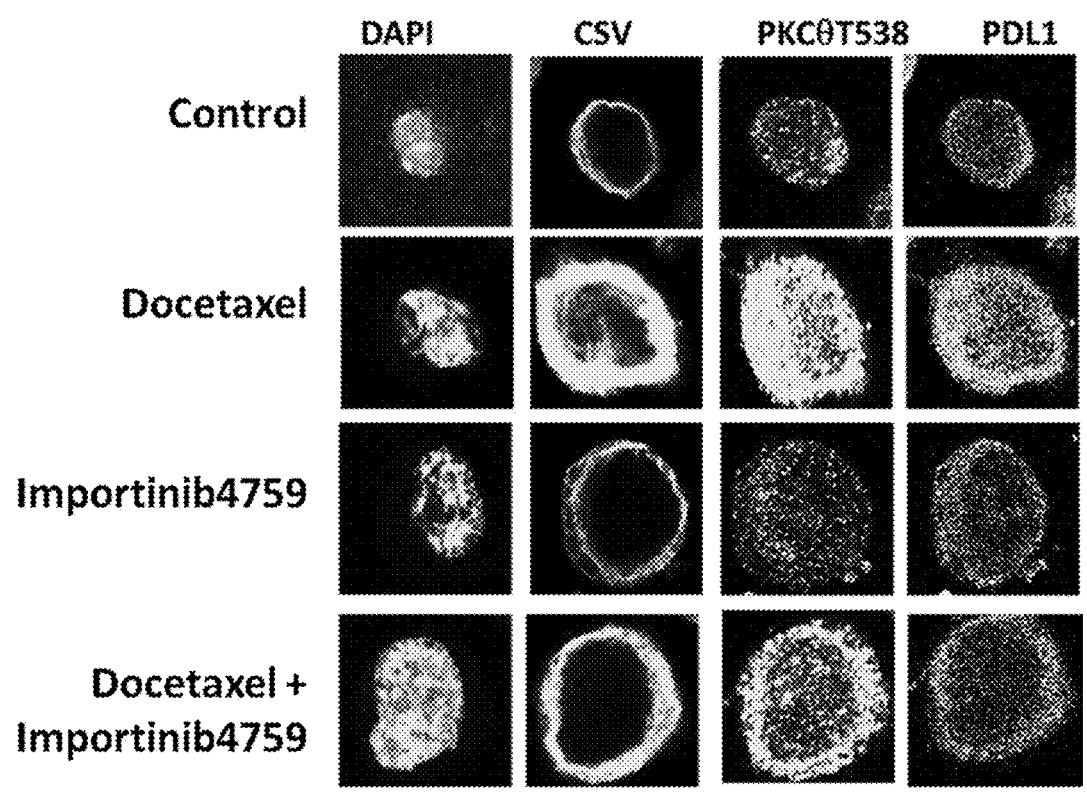
FIG. 12 Representation of confocal microscopy pictures showing the effect of importinib4759 and docetaxel on expression of cancer stem cell markers (CSV, PKC-θ and PDL1) in cells derived from a Balb/c-nude MDA-MB-231 xenograft breast cancer model.
Figure 13:
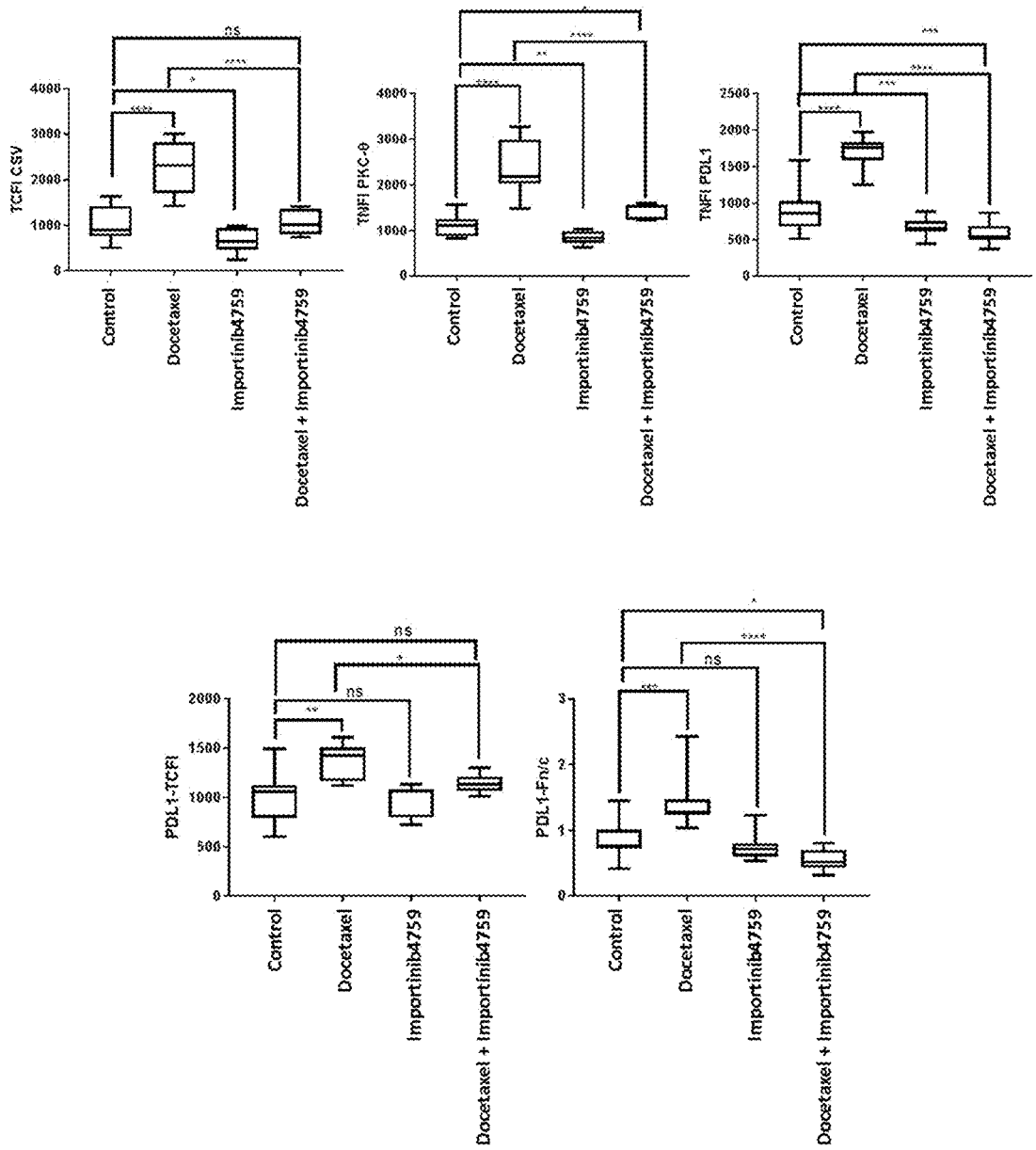
FIG. 13 Graphs presenting the effect of importinib4759 and docetaxel on nuclear (TNFI) and cytoplasmic (TCFI) expression of cancer stem cell markers (CSV, PKC-θ and PDL1) in cells derived from a Balb/c-nude MDA-MB-231 xenograft breast cancer model (n≥20 individual cells; data shown as mean±SE). **=p-value of ≤0.0001; *=p-value of ≤0.001; **=p-value of ≤0.01; *=p-value of ≤0.05; ns=p-value of ≥0.05.

Similarly, the administration of importinib4759_O1 reduced tumor volume over time, with the combination of importinib4759_O1 and docetaxel causing a marked reduction in tumor volume (FIG. 8; overall p=0.0079). Both the combination treatment and importinib4759_O1 treatment abrogated tumor volume in comparison to the control or docetaxel treatment alone. Both importinib4759_O1 treatment alone and in combination with docetaxel significantly abrogated the cancer stem cell population (FIG. 9; overall p=0.0286).

Example 8 Effect of Importinib4759 Inhibitor on the Expression of Cancer Stem Cell Markers in MDA-MB-231 Xenograft Breast Cancer Cells The effect of Importinib4759 on the expression of cancer stem cell markers in MDA-MB-231 xenograft breast cancer cells from Balb-c nude mice was evaluated using confocal laser scanning microscopy.

MDA-MB-231 xenograft breast cancer cells from Balb-c nude mice were treated and prepared as per the method of Example 7. Test compounds included control (saline), docetaxel (4 mg/kg), importinib4759 (40 mg/kg; synthesized in accordance with Example 1) or a combination of importinib4759 (40 mg/kg) and docetaxel (4 mg/kg). The single cell suspensions were fixed with 3.7% formaldehyde and permeabilized with 2% Triton-X-100 and were then probed with primary mouse antibodies to CSV, primary goat antibodies to PDL1 and primary rabbit antibodies to phosphorylated LSD1 (LSD1p; lysine-specific histone demethylase 1A) or PKC-θ followed by the corresponding secondary antibody conjugated to anti mouse Alexa-Fluor 568, anti-goat Alexa-Fluor 633 or anti-rabbit Alexa-Fluor 488. The cell nucleus was stained with anti-fade DAPI. TNFI (Total Nuclear Fluorescence Intensity) or TCFI (Total Cytoplasmic Fluorescence Intensity) values were calculated for at least 20 individual cells per sample. Data shown represent the mean±SE grouped into time point of collection.

Docetaxel treatment alone increased expression of cancer stem cell markers in surviving resistant cancer cells (FIGS. 10-13). Treatment of the cells with importinib4759, both alone and in combination with docetaxel, significantly abrogated expression of cancer stem cell markers (markers of aggressive metastatic cancer).

Example 9 Effect of Importinib4759 on Expression of Cancer Associated Fibroblast (CAF) and Macrophage Markers in MDA-MB-231 Xenograft Breast Cancer Cells The effect of Importinib4759 on the expression of cancer associated fibroblast (CAF) and macrophage in MDA-MB-231 xenograft breast cancer cells from Balb-c nude mice was evaluated using confocal laser scanning microscopy.

MDA-MB-231 xenograft breast cancer cells from Balb-c nude mice were treated and prepared as per the method of Example 7. Test compounds included control (saline), docetaxel (4 mg/kg), importinib4759 (40 mg/kg; synthesized in accordance with Example 1) or a combination of importinib4759 (40 mg/kg) and docetaxel (4 mg/kg). The single cell suspensions were fixed with 3.7% formaldehyde and permeabilized with 2% Triton-X-100 and were then probed with a set of CAF signature antibodies [primary mouse antibodies to FAP (fibroblast activation protein), primary goat antibodies to CCL2 (chemokine (C-C motif) ligand 2) and primary rabbit antibodies to LSD1 (lysine-specific histone demethylase 1A; a target of PKC-θ)] or M1 macrophage markers [primary mouse antibodies to CCR7 (C-C chemokine receptor type 7), primary goat antibodies to CD38 (cluster of differentiation 38) and primary rabbit antibodies to LSD1p (a target of PKC-θ)], followed by the corresponding secondary antibody conjugated to anti mouse Alexa-Fluor 568, anti-goat Alexa-Fluor 633 or anti-rabbit Alexa-Fluor 488. The cell nucleus was stained with anti-fade DAPI. TNFI or TCFI values were calculated for at least 20 individual cells per sample. Data shown represent the mean±SE grouped into time point of collection.

CAFs are responsible for creating a tumor microenvironment conducive to the induction of the cancer stem cell signature and promote tumorigenesis, metastasis and resistance.

Figure 14:
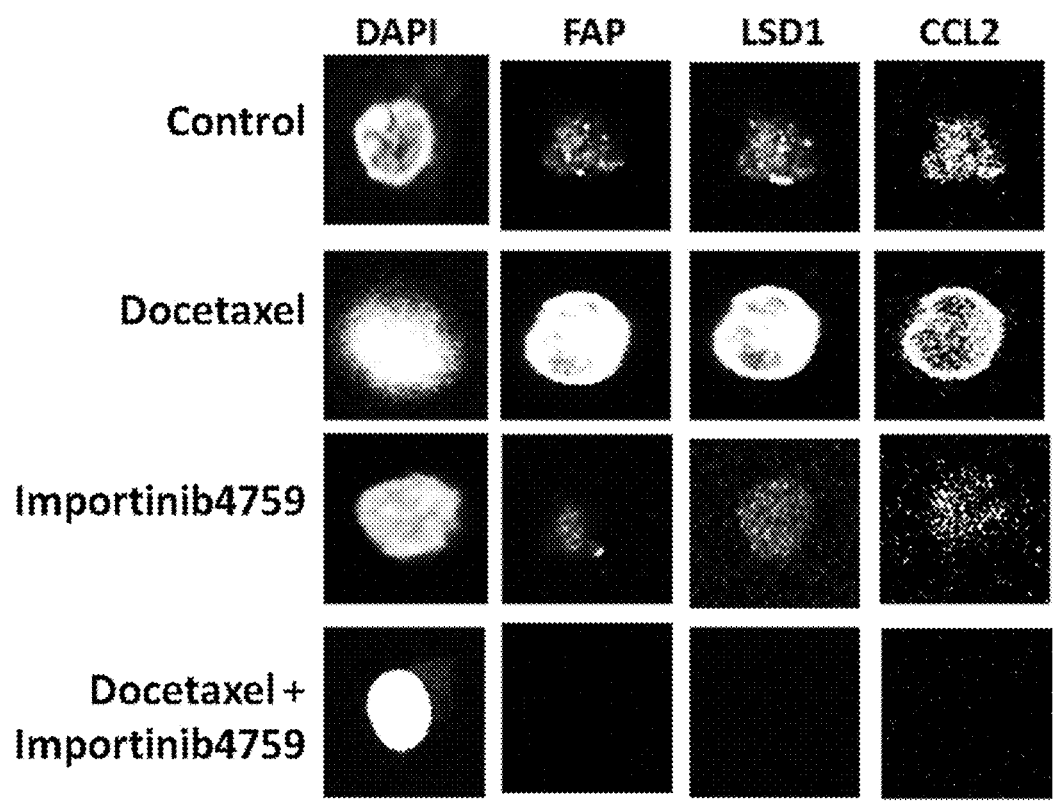
FIG. 14 Representation of confocal microscopy pictures showing the effect of importinib4759 and docetaxel on expression of CAF markers (FAP, LSD1 and CCL2) in cells derived from a Balb/c-nude MDA-MB-231 xenograft breast cancer model.
Figure 15:
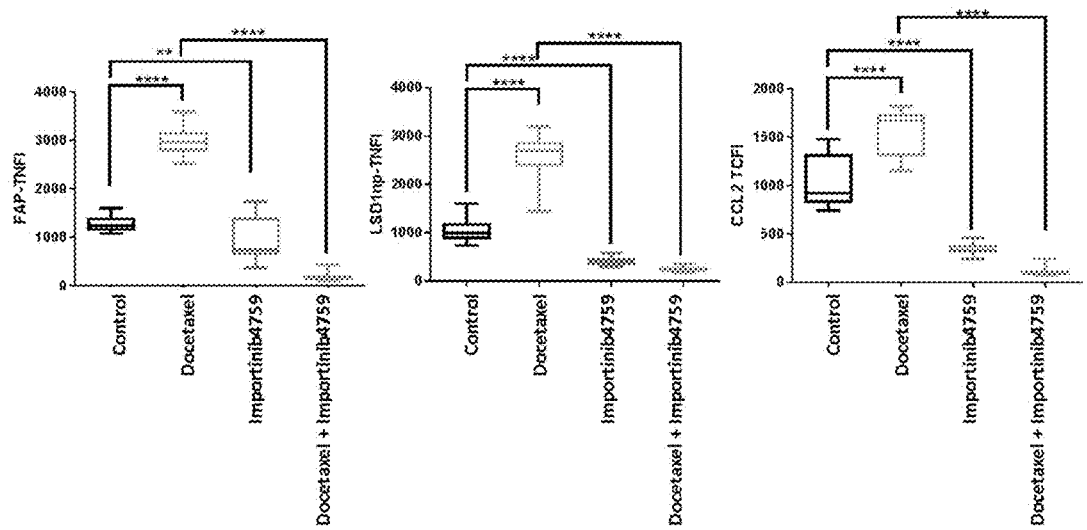
FIG. 15 Graphs presenting the effect of importinib4759 and docetaxel on nuclear and (TNFI) and cytoplasmic (TCFI) expression of CAF markers (FAP, LSD1 and CCL2) in cells derived from a Balb/c-nude MDA-MB-231 xenograft breast cancer model (n≥20 individual cells; data shown as mean±SE). **=p-value of ≤0.0001; *=p-value of ≤0.001; **=p-value of ≤0.01; *=p-value of ≤0.05; ns=p-value of ≥0.05.

Treatment with docetaxel alone significantly increased the expression of CAF markers [FAP, non-phosphorylated LSD1 (LSD1np) and CCL2] in surviving resistant cancer cells (FIGS. 14 and 15; p<0.0001 for all markers). Conversely, treatment with importinib4759 alone (FAP p=0.0018, LSD1np p<0.0001, CCL2 p<0.0001 relative to control) or in combination with docetaxel (p<0.0001 for all markers relative to control) abrogated expression of CAF markers.

Figure 16:
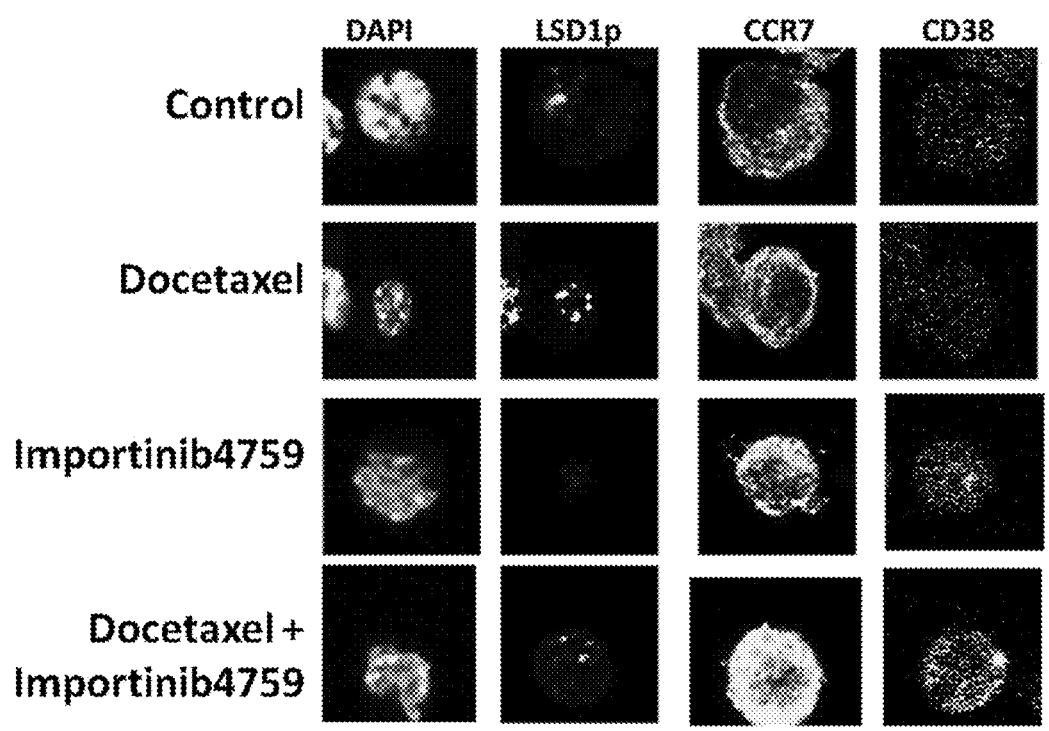
FIG. 16 Representation of confocal microscopy pictures showing the effect of importinib4759 and docetaxel on expression of M1 macrophage markers (LSD1p, CCR7 and CD38) in cells derived from a Balb/c-nude MDA-MB-231 xenograft breast cancer model.
Figure 17:
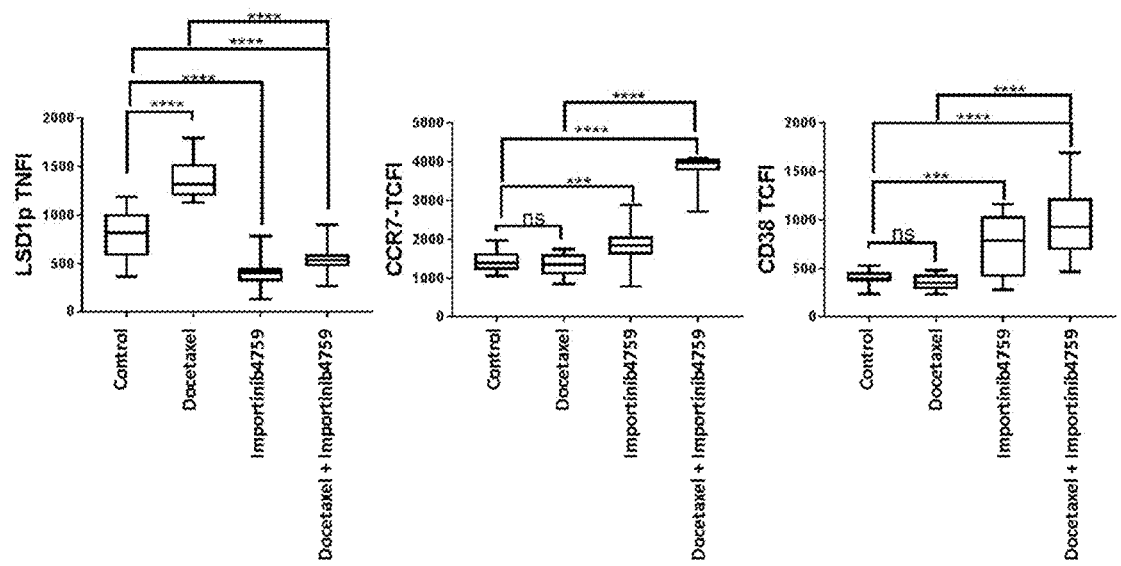
FIG. 17 Graphs presenting the effect of importinib4759 and docetaxel on nuclear and (TNFI) and cytoplasmic (TCFI) expression of M1 macrophage markers (LSD1p, CCR7 and CD38) in cells derived from a Balb/c-nude MDA-MB-231 xenograft breast cancer model (n≥20 individual cells; data shown as mean±SE). **=p-value of ≤0.0001; *=p-value of ≤0.001; **=p-value of ≤0.01; *=p-value of ≤0.05; ns=p-value of ≥0.05.

The expression of M1 macrophage markers is indicative of tumor immunity. The expression of the M1 macrophage markers CCR7 and CD38 was unaffected after docetaxel treatment (FIGS. 16 and 17; p=not significant for both markers). Following treatment with importinib4759 (LSD1p p<0.0001, CCR7 p<0.0001, CD38 p=0.0003 relative to control) and the combination of importinib4759 and docetaxel (LSD1p p<0.0001, CCR7 p<0.0001, CD38 p<0.0001), expression of the M1 macrophage markers was augmented.

The disclosure of every patent, patent application, and publication cited herein is hereby incorporated herein by reference in its entirety.

The claims defining the invention are as follows:

1. A method of altering at least one of (i) formation; (ii) proliferation; (iii) maintenance; (iv) epithelial to mesenchymal cell transition; or (v) mesenchymal to epithelial cell transition of a PKC-θ overexpressing cell, comprising contacting said PKC-θ overexpressing cell with an isolated or purified proteinaceous molecule represented by Formula I:

$$Z_1 X_1 X_2 X_3 X_4 ID X_5 PP X_6 X_7 X_8 X_9 X_{10} X_{11} Z_2 \quad (I)$$

wherein:

"$Z_1$" and "$Z_2$" are independently absent or are independently selected from at least one of a proteinaceous moiety comprising from about 1 to about 50 amino acid residues, and a protecting moiety;

"$X_1$" is absent or is selected from basic amino acid residues including R, K and modified forms thereof;

"$X_2$" and "$X_3$" are independently selected from basic amino acid residues including R, K and modified forms thereof;

"$X_4$" is selected from charged amino acid residues including R, K, D, E and modified forms thereof;

"$X_5$" is absent or is W or modified forms thereof;

"$X_6$" is selected from aromatic or basic amino acid residues including F, Y, W, R, K and modified forms thereof;

"$X_7$" is selected from basic amino acid residues including R, K and modified forms thereof;

"$X_8$" is absent or is P or modified forms thereof;

"$X_9$" is selected from basic amino acid residues including R, K and modified forms thereof;

"$X_{10}$" is selected from hydrophobic residues including V, L, I, M and modified forms thereof and P and modified forms thereof;

"$X_{11}$" is selected from basic amino acid residues including R, K and modified forms thereof.

2. The method according to claim 1, wherein the PKC-θ overexpressing cell is a cancer stem cell or a non-cancer stem cell tumor cell.

3. A method of treating or preventing a cancer in a subject, wherein the cancer comprises at least one PKC-θ overexpressing cell, comprising administering to the subject an isolated or purified proteinaceous molecule represented by Formula I as defined in claim 1.

4. The method according to claim 1, wherein "$X_1$" is absent or is R.

5. The method according to claim 1, wherein "$X_2$" is R.

6. The method according to claim 1, wherein "$X_3$" is K.

7. The method according to claim 1, wherein "$X_4$" is E or R.

8. The method according to claim 1, wherein "$X_5$" is absent or is W.

9. The method according to claim 1, wherein "$X_6$" is F or R.

10. The method according to claim 1, wherein "$X_7$" is R.

11. The method according to claim 1, wherein "$X_9$" is K.

12. The method according to claim 1, wherein "$X_{10}$" is V or P.

13. The method according to claim 1, wherein "$X_{11}$" is K.

14. The method according to claim 1, wherein "$Z_1$" is a proteinaceous molecule represented by Formula II:

$$X_{12}X_{13}X_{14}X_{15}X_{16} \quad (II)$$

wherein:

"$X_{12}$" is absent or is a protecting moiety;

"$X_{13}$" is absent or is selected from P and basic amino acid residues including R, K and modified forms thereof;

"$X_{14}$" is absent or is selected from P and basic amino acid residues including R, K and modified forms thereof;

"$X_{15}$" is absent or is selected from P and basic amino acid residues including R, K and modified forms thereof;

"$X_{16}$" is absent or is selected from P and basic amino acid residues including R, K and modified forms thereof.

15. The method according to claim 1, wherein "$Z_1$" and "$Z_2$" are absent.

16. The method according to claim 1, wherein the proteinaceous molecule of Formula I comprises an amino acid sequence represented by SEQ ID NO: 1 or 2:

```
                                    [SEQ ID NO: 1]
RKEIDPPFRPKVK
or
                                    [SEQ ID NO: 2]
RRKRIDWPPRRKPK.
```

17. The method according to claim 1, wherein the proteinaceous molecule of Formula I further comprises at least one membrane permeating moiety, wherein the membrane permeating moiety is a myristoyl group.

18. An isolated or purified proteinaceous molecule represented by Formula I:

$$Z_1X_1X_2X_3X_4IDX_5PPX_6X_7X_8X_9X_{10}X_{11}Z_2 \quad (I)$$

wherein:

"$Z_1$" and "$Z_2$" are independently absent or are independently selected from at least one of a proteinaceous moiety comprising from about 1 to about 50 amino acid residues, and a protecting moiety;

"$X_1$" is absent or is selected from basic amino acid residues including R, K and modified forms thereof;

"$X_2$" and "$X_3$" are independently selected from basic amino acid residues including R, K and modified forms thereof;

"$X_4$" is selected from charged amino acid residues including R, K, D, E and modified forms thereof;

"$X_5$" is absent or is W or modified forms thereof;

"$X_6$" is selected from aromatic or basic amino acid residues including F, Y, W, R, K and modified forms thereof;

"$X_7$" is selected from basic amino acid residues including R, K and modified forms thereof;

"$X_8$" is absent or is P or modified forms thereof;

"$X_9$" is selected from basic amino acid residues including R, K and modified forms thereof;

"$X_{10}$" is selected from hydrophobic residues including V, L, I, M and modified forms thereof and P or modified forms thereof;

"$X_{11}$" is selected from basic amino acid residues including R, K and modified forms thereof;

wherein the proteinaceous molecule is other than a proteinaceous molecule consisting of the amino acid sequence of SEQ ID NO: 1:

```
                                    [SEQ ID NO: 1]
RKEIDPPFRPKVK.
```

19. The proteinaceous molecule according to claim 18, wherein "$X_1$" is absent or is R.

20. The proteinaceous molecule according to claim 18, wherein "$X_2$" is R.

21. The proteinaceous molecule according to claim 18, wherein "$X_3$" is K.

22. The proteinaceous molecule according to claim 18, wherein "$X_4$" is E or R.

23. The proteinaceous molecule according to claim 18, wherein "$X_5$" is absent or is W.

24. The proteinaceous molecule according to claim 18, wherein "$X_6$" is F or R.

25. The proteinaceous molecule according to claim 18, wherein "$X_7$" is R.

26. The proteinaceous molecule according to claim 18, wherein "$X_9$" is K.

27. The proteinaceous molecule according to claim 18, wherein "$X_{10}$" is V or P.

28. The proteinaceous molecule according to claim 18, wherein "$X_{11}$" is K.

29. The proteinaceous molecule according to claim 18, wherein the proteinaceous molecule comprises the amino acid sequence of SEQ ID NO: 2:

```
                                    [SEQ ID NO: 2]
RRKRIDWPPRRKPK.
```

* * * * *

UNITED STATES PATENT AND TRADEMARK OFFICE
CERTIFICATE OF CORRECTION

PATENT NO. : 10,487,115 B2
APPLICATION NO. : 16/074690
DATED : November 26, 2019
INVENTOR(S) : Sudha Rao and Peter Milburn It is certified that error appears in the above-identified patent and that said Letters Patent is hereby corrected as shown below:

On the Title Page

Delete:
"Assignee: UNIVERSITY OF CANBERRA (Bruce, Australian Capital Territory, AU)"

And insert therefor:
-- Assignee: EpiAxis Therapeutics Pty Ltd. (Canberra, AU) --

Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 58

<210> SEQ ID NO 1
<211> LENGTH: 13
<212> TYPE: PRT
<213> ORGANISM: Artificial Sequence
<220> FEATURE:
<223> OTHER INFORMATION: Amino acid sequence corresponding to the
      nuclear localisation signal of PKC-theta

<400> SEQUENCE: 1

Arg Lys Glu Ile Asp Pro Pro Phe Arg Pro Lys Val Lys
1               5                   10
```

<210> SEQ ID NO 2
<211> LENGTH: 14
<212> TYPE: PRT
<213> ORGANISM: Artificial Sequence
<220> FEATURE:
<223> OTHER INFORMATION: Amino acid sequence corresponding to nuclear
      localisation signal motif

<400> SEQUENCE: 2

Arg Arg Lys Arg Ile Asp Trp Pro Pro Arg Arg Lys Pro Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 3

Tyr Gly Arg Lys Lys Arg Pro Gln Arg Arg Arg
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Cell penetrating peptide

<400> SEQUENCE: 4

Arg Arg Trp Arg Arg Trp Trp Arg Arg Trp Trp Arg Arg Trp Arg Arg
1               5                   10                  15

<210> SEQ ID NO 5
<211> LENGTH: 20
<212> TYPE: PRT
<213> ORGANISM: Artificial Sequence
<220> FEATURE:
<223> OTHER INFORMATION: Cell penetrating peptide

<400> SEQUENCE: 5

Cys Trp Lys Lys Lys Lys Lys Lys Lys Lys Lys Lys Lys Lys Lys Lys
1               5                   10                  15

Lys Lys Lys Lys
            20

<210> SEQ ID NO 6
<211> LENGTH: 40
<212> TYPE: PRT
<213> ORGANISM: Artificial Sequence
<220> FEATURE:
<223> OTHER INFORMATION: Cell penetrating peptide

<400> SEQUENCE: 6

Lys Lys Lys Lys Lys Lys Lys Lys Lys Lys Lys Lys Lys Lys Lys Lys
1               5                   10                  15

Lys Lys Trp Cys Cys Trp Lys Lys Lys Lys Lys Lys Lys Lys Lys Lys
                20                  25                  30

Lys Lys Lys Lys Lys Lys Lys Lys
            35                  40

<210> SEQ ID NO 7
<211> LENGTH: 26

```
<212> TYPE: PRT
<213> ORGANISM: Artificial Sequence
<220> FEATURE:
<223> OTHER INFORMATION: Cell penetrating peptide

<400> SEQUENCE: 7

Trp Thr Leu Asn Ser Ala Gly Tyr Leu Leu Gly Lys Ile Asn Leu Lys
1               5                   10                  15

Ala Leu Ala Ala Leu Ala Lys Lys Ile Leu
            20                  25

<210> SEQ ID NO 8
<211> LENGTH: 13
<212> TYPE: PRT
<213> ORGANISM: Artificial Sequence
<220> FEATURE:
<223> OTHER INFORMATION: Cell penetrating peptide

<400> SEQUENCE: 8

Gly Leu Phe Glu Ala Leu Glu Glu Leu Trp Glu Ala Lys
1               5                   10

<210> SEQ ID NO 9
<211> LENGTH: 46
<212> TYPE: PRT
<213> ORGANISM: Artificial Sequence
<220> FEATURE:
<223> OTHER INFORMATION: Cell penetrating peptide

<400> SEQUENCE: 9

Lys Lys Lys Lys Lys Lys Lys Lys Lys Lys Lys Lys Lys Lys Lys Lys
1               5                   10                  15

Gly Gly Cys Arg Gly Asp Met Phe Gly Cys Ala Lys Lys Lys Lys
            20                  25                  30

Lys Lys Lys Lys Lys Lys Lys Lys Lys Lys Arg Gly Asp
            35                  40                  45

<210> SEQ ID NO 10
<211> LENGTH: 25
<212> TYPE: PRT
<213> ORGANISM: Artificial Sequence
<220> FEATURE:
<223> OTHER INFORMATION: Cell penetrating peptide

<400> SEQUENCE: 10

Lys Lys Lys Lys Lys Lys Lys Lys Lys Lys Lys Lys Lys Lys Lys Lys
1               5                   10                  15

Gly Gly Cys Met Phe Gly Cys Gly Gly
            20                  25

<210> SEQ ID NO 11
<211> LENGTH: 31
<212> TYPE: PRT
<213> ORGANISM: Artificial Sequence
<220> FEATURE:
<223> OTHER INFORMATION: Cell penetrating peptide

<400> SEQUENCE: 11

Lys Lys Lys Lys Lys Lys Lys Lys Lys Lys Lys Lys Lys Lys Lys Lys
1               5                   10                  15

Ile Cys Arg Arg Ala Arg Gly Asp Asn Pro Asp Asp Arg Cys Thr
            20                  25                  30

<210> SEQ ID NO 12
```

```
<211> LENGTH: 22
<212> TYPE: PRT
<213> ORGANISM: Artificial Sequence
<220> FEATURE:
<223> OTHER INFORMATION: Cell penetrating peptide
<220> FEATURE:
<221> NAME/KEY: MISC_FEATURE
<222> LOCATION: (17)..(17)
<223> OTHER INFORMATION: Xaa is Asn or Asp
<220> FEATURE:
<221> NAME/KEY: MISC_FEATURE
<222> LOCATION: (17)..(17)
<223> OTHER INFORMATION: Xaa is Asn or Asp
<220> FEATURE:
<221> NAME/KEY: MISC_FEATURE
<222> LOCATION: (20)..(20)
<223> OTHER INFORMATION: Xaa is Asn or Asp
<220> FEATURE:
<221> NAME/KEY: MISC_FEATURE
<222> LOCATION: (21)..(21)
<223> OTHER INFORMATION: Xaa is Asn or Asp

<400> SEQUENCE: 12

Lys Lys Trp Lys Met Arg Arg Asn Gln Phe Trp Val Lys Val Gln Arg
1               5                   10                  15

Xaa Ala Lys Xaa Xaa Ala
            20

<210> SEQ ID NO 13
<211> LENGTH: 30
<212> TYPE: PRT
<213> ORGANISM: Artificial Sequence
<220> FEATURE:
<223> OTHER INFORMATION: Cell penetrating peptide

<400> SEQUENCE: 13

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Cell penetrating peptide

<400> SEQUENCE: 14

Ile Gly Arg Ile Asp Pro Ala Asn Gly Lys Thr Lys Tyr Ala Pro Lys
1               5                   10                  15

Phe Gln Asp Lys Ala Thr Arg Ser Asn Tyr Tyr Gly Asn Ser Pro Ser
            20                  25                  30

<210> SEQ ID NO 15
<211> LENGTH: 21
<212> TYPE: PRT
<213> ORGANISM: Artificial Sequence
<220> FEATURE:
<223> OTHER INFORMATION: Cell penetrating peptide

<400> SEQUENCE: 15

Lys Glu Thr Trp Trp Glu Thr Trp Trp Thr Glu Trp Ser Gln Pro Lys
1               5                   10                  15

Lys Lys Arg Lys Val
            20
```

```
<210> SEQ ID NO 16
<211> LENGTH: 12
<212> TYPE: PRT
<213> ORGANISM: Artificial Sequence
<220> FEATURE:
<223> OTHER INFORMATION: Cell penetrating peptide

<400> SEQUENCE: 16

Pro Leu Ala Glu Ile Asp Gly Ile Glu Leu Thr Tyr
1               5                   10

<210> SEQ ID NO 17
<211> LENGTH: 30
<212> TYPE: PRT
<213> ORGANISM: Artificial Sequence
<220> FEATURE:
<223> OTHER INFORMATION: Cell penetrating peptide

<400> SEQUENCE: 17

Lys Lys Lys Lys Lys Lys Lys Lys Lys Lys Lys Lys Lys Lys Lys
1               5                   10                  15

Gly Gly Pro Leu Ala Glu Ile Asp Gly Ile Glu Leu Gly Ala
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Cell penetrating peptide

<400> SEQUENCE: 18

Lys Lys Lys Lys Lys Lys Lys Lys Lys Lys Lys Lys Lys Lys Lys
1               5                   10                  15

Gly Gly Pro Leu Ala Glu Ile Asp Gly Ile Glu Leu Cys Ala
            20                  25                  30

<210> SEQ ID NO 19
<211> LENGTH: 28
<212> TYPE: PRT
<213> ORGANISM: Artificial Sequence
<220> FEATURE:
<223> OTHER INFORMATION: Cell penetrating peptide

<400> SEQUENCE: 19

Gly Ala Leu Phe Leu Gly Phe Leu Gly Gly Ala Ala Gly Ser Thr Met
1               5                   10                  15

Gly Ala Trp Ser Gln Pro Lys Ser Lys Arg Lys Val
            20                  25

<210> SEQ ID NO 20
<211> LENGTH: 28
<212> TYPE: PRT
<213> ORGANISM: Artificial Sequence
<220> FEATURE:
<223> OTHER INFORMATION: Cell penetrating peptide

<400> SEQUENCE: 20

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys
            20                  25

<210> SEQ ID NO 21
<211> LENGTH: 30
```

```
<212> TYPE: PRT
<213> ORGANISM: Artificial Sequence
<220> FEATURE:
<223> OTHER INFORMATION: Cell penetrating peptide

<400> SEQUENCE: 21

Leu Ala Arg Leu Leu Ala Arg Leu Leu Ala Arg Leu Leu Ala Arg Leu
1               5                   10                  15

Leu Ala Arg Leu Leu Ala Arg Leu Asn His Cys His His His
            20                  25                  30

<210> SEQ ID NO 22
<211> LENGTH: 16
<212> TYPE: PRT
<213> ORGANISM: Artificial Sequence
<220> FEATURE:
<223> OTHER INFORMATION: Cell penetrating peptide

<400> SEQUENCE: 22

Lys Leu Leu Lys Leu Leu Lys Leu Trp Leu Leu Lys Leu Leu Leu
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 23

Lys Lys Lys Lys Lys Lys Lys Lys Gly Gly Cys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 24

Lys Trp Lys Lys Lys Trp Lys Lys Gly Cys Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 25

Arg Trp Arg Arg Arg Trp Arg Arg Gly Gly Cys
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Cell penetrating peptide

<400> SEQUENCE: 26

Pro Lys Lys Lys Arg Lys Val
1               5
```

```
<210> SEQ ID NO 27
<211> LENGTH: 12
<212> TYPE: PRT
<213> ORGANISM: Artificial Sequence
<220> FEATURE:
<223> OTHER INFORMATION: Cell penetrating peptide

<400> SEQUENCE: 27

Pro Glu Val Lys Lys Lys Arg Lys Pro Glu Tyr Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Cell penetrating peptide

<400> SEQUENCE: 28

Thr Pro Pro Lys Lys Lys Arg Lys Val Glu Asp Pro
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Cell penetrating peptide

<400> SEQUENCE: 29

Gly Gly Gly Gly Pro Lys Lys Lys Arg Lys Val Gly Gly
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Cell penetrating peptide

<400> SEQUENCE: 30

Gly Gly Gly Phe Ser Thr Ser Leu Arg Ala Arg Lys Ala
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Cell penetrating peptide

<400> SEQUENCE: 31

Cys Lys Lys Lys Lys Lys Lys Ser Glu Asp Glu Tyr Pro Tyr Val Pro
1               5                   10                  15

Asn

<210> SEQ ID NO 32
<211> LENGTH: 28
<212> TYPE: PRT
<213> ORGANISM: Artificial Sequence
<220> FEATURE:
<223> OTHER INFORMATION: Cell penetrating peptide

<400> SEQUENCE: 32

Cys Lys Lys Lys Lys Lys Lys Lys Ser Glu Asp Glu Tyr Pro Tyr Val
1               5                   10                  15
```

Pro Asn Phe Ser Thr Ser Leu Arg Ala Arg Lys Ala
            20                  25

<210> SEQ ID NO 33
<211> LENGTH: 25
<212> TYPE: PRT
<213> ORGANISM: Artificial Sequence
<220> FEATURE:
<223> OTHER INFORMATION: Cell penetrating peptide

<400> SEQUENCE: 33

Leu Val Arg Lys Lys Arg Lys Thr Glu Glu Glu Ser Pro Leu Lys Asp
1               5                   10                  15

Lys Asp Ala Lys Lys Ser Lys Gln Glu
            20                  25

<210> SEQ ID NO 34
<211> LENGTH: 30
<212> TYPE: PRT
<213> ORGANISM: Artificial Sequence
<220> FEATURE:
<223> OTHER INFORMATION: Cell penetrating peptide

<400> SEQUENCE: 34

Lys Lys Lys Lys Lys Lys Lys Lys Lys Lys Lys Lys Lys Lys Lys Lys
1               5                   10                  15

Lys Lys Lys Lys Lys Lys Gly Gly Lys Lys Lys Lys Lys Lys
            20                  25                  30

<210> SEQ ID NO 35
<211> LENGTH: 13
<212> TYPE: PRT
<213> ORGANISM: Artificial Sequence
<220> FEATURE:
<223> OTHER INFORMATION: Cell penetrating peptide

<400> SEQUENCE: 35

Gly Arg Lys Lys Arg Arg Gln Arg Arg Arg Pro Pro Gln
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Cell penetrating peptide

<400> SEQUENCE: 36

Arg Gln Ile Lys Ile Trp Phe Gln Asn Arg Arg Met Lys Trp Lys Lys
1               5                   10                  15

<210> SEQ ID NO 37
<211> LENGTH: 21
<212> TYPE: PRT
<213> ORGANISM: Artificial Sequence
<220> FEATURE:
<223> OTHER INFORMATION: Cell penetrating peptide

<400> SEQUENCE: 37

Thr Arg Ser Ser Arg Ala Gly Leu Gln Phe Pro Val Gly Arg Val His
1               5                   10                  15

Arg Leu Leu Arg Lys
            20

<210> SEQ ID NO 38

```
<211> LENGTH: 13
<212> TYPE: PRT
<213> ORGANISM: Artificial Sequence
<220> FEATURE:
<223> OTHER INFORMATION: Cell penetrating peptide

<400> SEQUENCE: 38

Lys Arg Val Ser Arg Asn Lys Ser Glu Lys Lys Arg Arg
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Cell penetrating peptide

<400> SEQUENCE: 39

Lys Leu Ala Leu Lys Leu Ala Leu Lys Ala Leu Lys Ala Ala Leu Lys
1               5                   10                  15

Leu Ala

<210> SEQ ID NO 40
<211> LENGTH: 16
<212> TYPE: PRT
<213> ORGANISM: Artificial Sequence
<220> FEATURE:
<223> OTHER INFORMATION: Cell penetrating peptide

<400> SEQUENCE: 40

Ala Ala Val Ala Leu Leu Pro Ala Val Leu Leu Ala Leu Leu Ala Pro
1               5                   10                  15

<210> SEQ ID NO 41
<211> LENGTH: 6
<212> TYPE: PRT
<213> ORGANISM: Artificial Sequence
<220> FEATURE:
<223> OTHER INFORMATION: Cell penetrating peptide

<400> SEQUENCE: 41

Val Pro Met Leu Lys Glu
1               5

<210> SEQ ID NO 42
<211> LENGTH: 5
<212> TYPE: PRT
<213> ORGANISM: Artificial Sequence
<220> FEATURE:
<223> OTHER INFORMATION: Cell penetrating peptide

<400> SEQUENCE: 42

Val Pro Met Leu Lys
1               5

<210> SEQ ID NO 43
<211> LENGTH: 5
<212> TYPE: PRT
<213> ORGANISM: Artificial Sequence
<220> FEATURE:
<223> OTHER INFORMATION: Cell penetrating peptide

<400> SEQUENCE: 43

Pro Met Leu Lys Glu
1               5
```

```
<210> SEQ ID NO 44
<211> LENGTH: 4
<212> TYPE: PRT
<213> ORGANISM: Artificial Sequence
<220> FEATURE:
<223> OTHER INFORMATION: Cell penetrating peptide

<400> SEQUENCE: 44

Pro Met Leu Lys
1

<210> SEQ ID NO 45
<211> LENGTH: 28
<212> TYPE: PRT
<213> ORGANISM: Artificial Sequence
<220> FEATURE:
<223> OTHER INFORMATION: Cell penetrating peptide

<400> SEQUENCE: 45

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 46
<211> LENGTH: 18
<212> TYPE: PRT
<213> ORGANISM: Artificial Sequence
<220> FEATURE:
<223> OTHER INFORMATION: Cell penetrating peptide

<400> SEQUENCE: 46

Leu Leu Ile Ile Leu Arg Arg Arg Ile Arg Lys Gln Ala His Ala His
1               5                   10                  15

Ser Lys

<210> SEQ ID NO 47
<211> LENGTH: 21
<212> TYPE: PRT
<213> ORGANISM: Artificial Sequence
<220> FEATURE:
<223> OTHER INFORMATION: Cell penetrating peptide

<400> SEQUENCE: 47

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 48
<211> LENGTH: 18
<212> TYPE: PRT
<213> ORGANISM: Artificial Sequence
<220> FEATURE:
<223> OTHER INFORMATION: Cell penetrating peptide

<400> SEQUENCE: 48

Arg Gly Gly Arg Leu Ser Tyr Ser Arg Arg Arg Phe Ser Thr Ser Thr
1               5                   10                  15

Gly Arg

<210> SEQ ID NO 49
<211> LENGTH: 27
<212> TYPE: PRT
<213> ORGANISM: Artificial Sequence
```

```
<220> FEATURE:
<223> OTHER INFORMATION: Cell penetrating peptide

<400> SEQUENCE: 49

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 50
<211> LENGTH: 21
<212> TYPE: PRT
<213> ORGANISM: Artificial Sequence
<220> FEATURE:
<223> OTHER INFORMATION: Cell penetrating peptide

<400> SEQUENCE: 50

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 51
<211> LENGTH: 21
<212> TYPE: PRT
<213> ORGANISM: Artificial Sequence
<220> FEATURE:
<223> OTHER INFORMATION: Cell penetrating peptide
<220> FEATURE:
<221> NAME/KEY: MISC_FEATURE
<222> LOCATION: (21)..(21)
<223> OTHER INFORMATION: Xaa is cysteamide

<400> SEQUENCE: 51

Gly Leu Trp Arg Ala Leu Trp Arg Leu Leu Arg Ser Leu Trp Arg Leu
1               5                   10                  15

Leu Trp Arg Ala Xaa
            20

<210> SEQ ID NO 52
<211> LENGTH: 15
<212> TYPE: PRT
<213> ORGANISM: Artificial Sequence
<220> FEATURE:
<223> OTHER INFORMATION: Cell penetrating peptide

<400> SEQUENCE: 52

Ser Asp Leu Trp Glu Met Met Met Val Ser Leu Ala Cys Gln Tyr
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: Cell penetrating peptide

<400> SEQUENCE: 53

Thr Ser Pro Leu Asn Ile His Asn Gly Gln Lys Leu
1               5                   10

<210> SEQ ID NO 54
<211> LENGTH: 26
<212> TYPE: PRT
<213> ORGANISM: Artificial Sequence
<220> FEATURE:
```

```
<223> OTHER INFORMATION: Cell penetrating peptide

<400> SEQUENCE: 54

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 55
<211> LENGTH: 16
<212> TYPE: PRT
<213> ORGANISM: Artificial Sequence
<220> FEATURE:
<223> OTHER INFORMATION: Cell penetrating peptide

<400> SEQUENCE: 55

Arg Val Ile Arg Val Trp Phe Gln Asn Lys Arg Cys Lys Asp Lys Lys
1               5                   10                  15

<210> SEQ ID NO 56
<211> LENGTH: 13
<212> TYPE: PRT
<213> ORGANISM: Artificial Sequence
<220> FEATURE:
<223> OTHER INFORMATION: Amino acid sequence corresponding to the
      nuclear localisation signal of PKC-beta1

<400> SEQUENCE: 56

Arg Lys Glu Ile Gln Pro Pro Tyr Lys Pro Lys Ala Arg
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Amino acid sequence corresponding to the
      nuclear localisation signal of PKC-epsilon

<400> SEQUENCE: 57

Lys Lys Ile Lys Pro Pro Phe Lys Pro Arg Ile Lys Thr Lys Arg
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: Amino acid sequence corresponding to the
      nuclear localisation signal of PKC-delta

<400> SEQUENCE: 58

Lys Arg Arg Leu Glu Pro Pro Phe Arg Pro Lys Val Lys
1               5                   10
```